(12) United States Patent
Meck et al.

(10) Patent No.: US 10,545,120 B2
(45) Date of Patent: Jan. 28, 2020

(54) SYSTEMS AND METHODS FOR PREDICTIVE DIAGNOSTICS FOR MECHANICAL SYSTEMS

(71) Applicant: John Crane UK Ltd., Slough, Berkshire (GB)

(72) Inventors: Klaus-Dieter Meck, Manchester (GB); Amrat Parmar, Bracknell (GB); David Unsworth, Haddington (GB)

(73) Assignee: JOHN CRANE UK LTD., Berkshire (GB)

( * ) Notice: Subject to any disclaimer, the term of this patent is extended or adjusted under 35 U.S.C. 154(b) by 182 days.

(21) Appl. No.: 15/440,764

(22) Filed: Feb. 23, 2017

(65) Prior Publication Data

US 2017/0241955 A1 Aug. 24, 2017

Related U.S. Application Data

(60) Provisional application No. 62/302,458, filed on Mar. 2, 2016, provisional application No. 62/302,451, filed
(Continued)

(51) Int. Cl.
*G01N 29/14* (2006.01)
*G01M 3/26* (2006.01)
*G07C 3/00* (2006.01)

(52) U.S. Cl.
CPC .............. *G01N 29/14* (2013.01); *G01M 3/26* (2013.01); *G07C 3/00* (2013.01)

(58) Field of Classification Search
CPC .. G01N 29/14; G01N 29/326; G01N 29/4436; G01M 3/26; G01M 13/005; G07C 3/00
See application file for complete search history.

(56) References Cited

U.S. PATENT DOCUMENTS 3,508,758 A 4/1970 Strub
4,389,849 A 6/1983 Gasser et al.
(Continued)

FOREIGN PATENT DOCUMENTS

DE 102008051176 A1 4/2010
EP 0209862 A2 1/1987
(Continued)

OTHER PUBLICATIONS

Search Report and Written Opinion dated Feb. 12, 2013 for PCT Application No. PCT/GB2011/001672, 23 pages.
(Continued)

*Primary Examiner* — Manuel L Barbee
(74) *Attorney, Agent, or Firm* — Cantor Colburn LLP

(57) ABSTRACT

A predictive diagnostics system for monitoring mechanical seals. The system autonomously detects a loss of lubrication within a sliding seal interface of a mechanical seal, the system including a loss of lubrication failure mode logic module configured to monitor data sensed by one or more sensors and diagnose conditions relating to a loss of lubrication within the sliding seal interface, and a plurality of other failure mode logic modules configured to monitor data sensed by the one or more sensors and diagnose conditions relating to specific types of mechanical failures known to occur in mechanical seal systems, the loss of lubrication failure mode logic module configured to determine which of the plurality of other failure mode logic modules are activated during the diagnosis of conditions related to a loss of lubrication within the sliding seal interface.

13 Claims, 12 Drawing Sheets

Related U.S. Application Data on Mar. 2, 2016, provisional application No. 62/298,851, filed on Feb. 23, 2016, provisional application No. 62/298,839, filed on Feb. 23, 2016, provisional application No. 62/298,848, filed on Feb. 23, 2016, provisional application No. 62/298,814, filed on Feb. 23, 2016.

(56) References Cited

U.S. PATENT DOCUMENTS

| | | | |
|---|---|---|---|
| 4,493,042 A | 1/1985 | Shima et al. |
| 4,613,285 A | 9/1986 | Sato et al. |
| 4,643,437 A | 2/1987 | Salant et al. |
| 4,691,276 A | 9/1987 | Miller et al. |
| 4,751,657 A | 6/1988 | Imam et al. |
| 4,988,979 A | 1/1991 | Sasaki et al. |
| 5,063,993 A | 11/1991 | Huston |
| 5,064,205 A | 11/1991 | Whitford |
| 5,076,589 A | 12/1991 | Marsi |
| 5,152,536 A | 10/1992 | Bardas |
| 5,170,359 A | 12/1992 | Sax et al. |
| 5,291,032 A | 3/1994 | Vali et al. |
| 5,327,920 A | 7/1994 | Gerard et al. |
| 5,412,977 A | 5/1995 | Schmohl et al. |
| 5,544,080 A | 8/1996 | Kobayashi et al. |
| 5,700,013 A | 12/1997 | Baty |
| 5,713,576 A | 2/1998 | Wasser et al. |
| 5,737,433 A | 4/1998 | Gardner |
| 5,755,372 A | 5/1998 | Cimbura, Sr. |
| 6,065,345 A * | 5/2000 | Holenstein ............ F04D 29/128 73/579 |
| 6,082,737 A | 7/2000 | Williamson et al. |
| 6,098,022 A | 8/2000 | Sonnichsen et al. |
| 6,345,954 B1 | 2/2002 | Al-Himyary et al. |
| 6,394,764 B1 | 5/2002 | Samurin |
| 6,575,621 B1 | 6/2003 | Zlochin |
| 6,626,436 B2 | 9/2003 | Pecht et al. |
| 6,715,985 B2 | 4/2004 | Delrahim et al. |
| 6,775,642 B2 | 8/2004 | Remboski et al. |
| 6,981,513 B2 | 1/2006 | Krywitsky |
| 7,025,559 B2 | 4/2006 | Loy et al. |
| 7,272,525 B2 | 9/2007 | Bennett et al. |
| 7,442,291 B1 | 10/2008 | Discenzo et al. |
| 7,640,139 B2 | 12/2009 | Sahara et al. |
| 7,854,584 B2 | 12/2010 | Lusted et al. |
| 8,651,801 B2 | 2/2014 | Shamseldin et al. |
| 9,145,783 B2 | 9/2015 | Delrahim et al. |
| 9,476,860 B2 | 10/2016 | Meck et al. |
| 2004/0112136 A1 | 6/2004 | Terry et al. |
| 2006/0196057 A1 | 9/2006 | So |
| 2008/0033695 A1 | 2/2008 | Sahara et al. |
| 2009/0287430 A1 | 11/2009 | Atoji et al. |
| 2009/0290971 A1 | 11/2009 | Shamseldin et al. |
| 2010/0101310 A1 | 4/2010 | Perie |
| 2010/0161255 A1 | 6/2010 | Mian et al. |
| 2014/0161587 A1 | 6/2014 | Shamseldin et al. |
| 2014/0182381 A1 | 7/2014 | Comeaux et al. |

FOREIGN PATENT DOCUMENTS

| | | |
|---|---|---|
| EP | 0297729 A2 | 1/1989 |
| EP | 0317322 A2 | 5/1989 |
| EP | 0800028 A1 | 8/1997 |
| EP | 0997714 A2 | 5/2000 |
| EP | 1286056 B1 | 10/2005 |
| EP | 2031386 A1 | 3/2009 |
| GB | 2190198 A | 11/1987 |
| JP | 5-164412 A | 6/1993 |
| WO | WO 99/59113 A2 | 11/1999 |
| WO | WO 01/033208 A1 | 5/2001 |
| WO | WO 2015/009805 A1 | 1/2015 |

OTHER PUBLICATIONS

Search Report dated Apr. 2, 2012 for EP Application No. 09761441.8, 8 pages.
The Seal Report, Jul. 12, 2002, 3 pages, vol. 1, Issue 3, John Crane Lemco, Tulsa, Oklahoma.
Search Report and Written Opinion dated May 9, 2009 for PCT Application No. PCT/US2009/044627, 9 pages.
Search Report and Written Opinion dated Oct. 9, 2012 for PCT Application No. PCT/US2012/049196, 13 pages.
Office Action dated Jul. 31, 2015 for Australian Application No. 2014240372, 2 pages.
Office Action dated Jan. 21, 2016 for Canadian Application No. 2,725,168, 4 pages.
Search Report and Written Opinion dated May 23, 2017 for PCT Application No. PCT/US2017/019139, 26 pages.
EPO Search Report for International Application No. 17757209.6 dated Sep. 11, 2019, 7 pages.
Juha Miettinen et al, "Acoustic Emission in Monitoring Sliding Contact Behaviour", Wear Wear, Jan. 1, 1995, pp. 181-183.

* cited by examiner

SYSTEMS AND METHODS FOR PREDICTIVE DIAGNOSTICS FOR MECHANICAL SYSTEMS

RELATED APPLICATIONS

The present application claims the benefit of U.S. Provisional Application No. 62/298,814 filed Feb. 23, 2016, U.S. Provisional Application No. 62/298,839 filed Feb. 23, 2016, U.S. Provisional Application No. 62/298,848 filed Feb. 23, 2016, U.S. Provisional Application No. 62/298,851 filed Feb. 23, 2016, U.S. Provisional Application No. 62/302,458 filed Mar. 2, 2016, and U.S. Provisional Application No. 62/302,451 filed Mar. 2, 2016, each of which is incorporated herein by reference in its entirety.

TECHNICAL FIELD

The present disclosure relates generally to mechanical seal systems. More particularly, the present disclosure relates to a system configured to detect operating conditions, provide real-time health assessments and predictive diagnostics for mechanical seal systems.

BACKGROUND

A mechanical seal is a device configured to provide a sealing interface between a static housing and rotating shaft of a device, such as a pump, mixer or the like, for the purpose of inhibiting fluid within the device from escaping and/or external contaminants from entering the device. Mechanical seals are employed in a wide variety of industrial applications, processing media and operating conditions, where a gap between a rotating shaft and a static housing has to be sealed.

Referring to FIG. 1, a cross-sectional view of a mechanical seal 100 of the prior art is depicted. In this depiction, the mechanical seal 100 is configured to inhibit the flow of fluid and contaminants through a gap 102 between a stationary housing 104 and a rotating shaft 106. The mechanical seal 100 is generally comprised of an annular stationary ring 108 (also known as a primary ring) and annular rotating ring 110 (also known as a mating ring), a pair of seals or glands 112, 114 (which are generally, but certainly not limited to, elastomeric sealing elements such as O-rings), and a biasing member 116. While the mechanical seal 100 depicted in FIG. 1 comprises a single pair of sealing rings 108 and 110, various mechanical seals known in the art can comprise additional sealing interfaces, such as for example the double seal embodiments disclosed in U.S. Pat. No. 8,857,818 (which is assigned to the Applicant of the present application), the contents of which are incorporated by reference herein.

In operation, the annular stationary ring 108 remains fixed in position relative to the housing 104. Gland 112 is positioned between the annular stationary ring 108 and the housing 104 to inhibit the flow of fluid between these components. Annular rotating ring 110 rotates with the rotating shaft 106. Gland 114 is positioned between the annular rotating ring 110 and the rotating shaft 106 to inhibit the flow of fluid between these components.

Both the annular stationary ring 108 and the annular rotating ring 110 include smooth, contacting seal faces 109, 111, thereby forming a sliding seal interface 118. Accordingly, use of the mechanical seal 100 enables the radial gap 102—where fluid would normally escape—to be sealed by a flat, sliding seal interface 118 that is perpendicular to the rotating shaft 106, and therefore much easier to seal.

A biasing member 116, such as one or more coil springs and/or a bellows arrangement, can be positioned between a boss 120 on the rotating shaft 106 and the gland 114 and/or annular rotating ring 110 to urge the floating annular rotating ring 110 towards the annular stationary ring 108. In this manner, the biasing member 116 aids in maintaining contact between contact seal faces 109, 111 by accommodating small shaft deflections, shaft movement due to bearing tolerances and out of perpendicular alignment due to manufacturing tolerances.

Because annular rotating ring 110 rotates relative to annular stationary ring 108, there is naturally some wear on the seal faces 109, 111 during operation. In particular, wear of the sliding seal interface 118 can be accelerated in the presence of friction and heat generation. Excessive wear of the seal faces 109, 111 ultimately leads to failure of the mechanical seal 100.

To slow the rate of wear, often a lubricant, commonly referred to as a lubricating fluid or barrier fluid, is introduced into the seal interface 118. The lubricating fluid can be the fluid to be sealed, or it can be another barrier fluid introduced into the seal interface 118. In another example, the seal interface can be lubricated by a dry gas, such as a vapor of the sealed product, air or nitrogen. Maintaining the proper film thickness and flow of the lubricant within the seal interface 118 is an important aspect in minimizing the wear of the seal faces 109, 111. Accordingly, the geometry of the seal faces 109, 111 and the width of gap 102 are precisely controlled in these types of mechanical seals, as they play an important role in determining the film thickness and flow of the lubricant.

More advanced mechanical seal systems can include multiple mechanical seals, such as a dual or double mechanical seal. Such mechanical seal systems can be provided with more than a single lubricating fluid. For example, in some double seal systems, the first mechanical seal is lubricated by a vapor of the sealed product, and the second mechanical seal is lubricated with another liquid or gas compatible with the sealed product. In some cases, the lubricating fluid of the second mechanical seal can be maintained at a higher pressure to further minimize leaking of the sealed product to the atmosphere.

Mechanical seal systems, therefore, can include not only the mechanical seals themselves, but also seal support systems such as an external reservoir, a bladder or piston accumulator for liquid lubricated seals, and a gas treatment unit (GTU) for a gas conditioning unit (GCU) for gas lubricated seals. These units can include components that provide appropriate filtration, flow management, heating, cooling, and other conditioning of the lubricating fluids. Mechanical seal systems can also include piping, tubing, and other connective units needed to appropriately manage fluid flow across the seal, as well as the housing and/or the device that the mechanical seal is installed in relation to.

As with all mechanical systems, eventually the annular stationary ring 108 and the annual rotating ring 110 will wear out and need to be replaced. In some cases, the components of the mechanical seal 100 will simply reach the end of their useful life. In other cases, certain conditions will hasten wear on the components within the mechanical seal 100. Some of these conditions include misinstallation of seal components or improper seal selection, the seal faces opening during operation as a result of axial misalignment or improper loading, flashing (liquid to vapor transition that causes pulsating leakage and chatter of the seal), cavitation, or environmental conditions which can lead to a collapse of the thin film of lubricant.

Efficient operation and maintenance of rotating equipment is essential to maximize production capacity and minimize downtime. Moreover, unexpected catastrophic equipment failure can result in injury to personnel. Fortunately, in many cases the mechanical seal system will begin to show signs of distress in advance of a catastrophic failure, and in some cases indicate the remaining useful life of the components.

Conventional equipment monitoring is most often affected by a person who periodically visits the equipment, to make observations of noise and leaks, and take vibration readings with an accelerometer. The gathered information can then be compared with the historical data on the equipment to detect trends to indicate the overall health of the mechanical seal 100. Various methods for condition monitoring and diagnostics are discussed in International Standards Organization (ISO) 17359:2011, CONDITION MONITORING AND DIAGNOSTICS OF MACHINES—GENERAL GUIDELINES, and ISO 13381-1:2015, CONDITION MONITORING AND DIAGNOSTICS OF MACHINES—PROGNOSTICS, the contents of which are incorporated by reference herein.

One problem with this procedure is the time and labor costs involved. Another problem is the fact that the equipment is not constantly monitored, thereby enabling acute conditions, such as flashing, cavitation, and the negative effects of certain environmental conditions to occur without warning.

More advanced monitoring systems may employ one or more sensors that enable monitoring of the equipment and mechanical seal 100 in real-time. These sensors can include, for example, temperature sensors, pressure transducers, and accelerometers. Such sensors can be intrusive, requiring permanent or temporary insertion of a probe or sensor within the stationary housing 104, or they can be non-intrusive and capable of detecting sensed data from the exterior of stationary housing 104, or other components of the mechanical seal system. Such systems are particularly useful in applications where the equipment to be monitored is in a hazardous location or access to such equipment is generally impeded. Examples of such systems are disclosed in U.S. Pat. Nos. 6,082,737 and 6,325,377; and U.S. Patent Publ. Nos. 2013/0275056 and 2014/0161587 (all assigned to the Applicant of the present application), the contents of which are incorporated by reference herein.

Other systems, such as those disclosed in, for example, U.S. Pat. Nos. 8,651,801 and 9,145,783 (assigned to the Applicant of the present application), the contents of which are incorporated by reference herein, can further provide monitoring of the device, such as a pump, mixer or the like, that the mechanical seal is installed in relation to. Such advanced monitoring systems can provide limited amounts of control of the mechanical seal, seal support system or other components, in response to the monitored conditions. For example, the monitoring system includes a control algorithm configured to automatically mitigate the effects of a mechanical seal malfunction by adjusting certain operating parameters of the mechanical seal system.

In some cases, the various sensors of the monitoring system are installed to aid in identifying one or more previously identified ways in which the mechanical seal system may fail. The various ways in which a mechanical seal system may fail may be determined through a process referred to as Failure Modes and Effects Analysis (FMEA). FMEA is a step-by-step approach for identifying all of the possible failures in a mechanical seal system design. The term "failure modes" refers to the ways, or modes, in which the mechanical seal system might fail, a failure meaning any type of error or defect which may adversely affect the performance and/or longevity of the mechanical seal system.

Once the possible failure modes in a mechanical seal system have been identified, the effects of the failure modes are analyzed through a process referred to as "effects analysis" in order to gain an understanding of the consequences of the identified failure modes. Based on the effects analysis, the failure modes are prioritized according to the severity of their consequences, how frequently they are likely to occur, and how easily they can be detected.

The overall purpose of the FMEA is to take actions to eliminate or reduce failures, beginning with the highest priority failure mode. Accordingly, FMEA is typically used during the design phase to insulate against anticipated failure modes; however, it may also be used during operation. FMEA is discussed in International Electrotechnical Commission (IEC) Standard 60812:2006: ANALYSIS TECHNIQUES FOR SYSTEM RELIABILITY—PROCEDURE FOR FAILURE MODE AND EFFECTS ANALYSIS (FMEA), the contents of which are incorporated by reference herein.

When FMEA of a particular mechanical seal system reveals a high priority failure mode, certain operating conditions can be monitored through an advanced monitoring system to aid in determining whether the failure mode is occurring, or is about to occur. In particular, an expert in the field of mechanical seal systems, such as a designer, engineer or technician, based on their experience, can set a particular threshold or limit for a given operating condition relating to the high priority failure mode. Thereafter, during operation, an operator can be alerted if the threshold or limit of the monitored condition is exceeded.

Unfortunately, the information provided by the individual sensors of an advanced monitoring system in isolation has in some cases proved insufficient to make conclusive determinations about the overall health of the mechanical seal system. For example, a particular operating condition exceeding a predefined threshold or limit may indicate that a particular failure mode is occurring, but based on other operating conditions, the exceeded threshold or limit may also be an indication of a wholly different type of failure or event. Complex mechanical seal systems are known to experience failures for multiple interrelated reasons. Accordingly, the advanced monitoring systems developed to date can require a human operator with a requisite level of knowledge of the monitored mechanical seal system in order to properly diagnose failures and the overall health of the mechanical seal system.

Human operators have the advantage of being able to reason in the abstract and potentially pull information from their experience, but a human operator's effectiveness can be hampered by their inability to digest large amounts of sensor data. For example, in some situations, relevant data may be inadvertently ignored by the human operator, resulting in an improper diagnosis. In other situations, a delay in making a decision about the health of the mechanical seal system may lead to a scenario in which it is no longer possible to avoid an impending failure, whereas had the decision been made earlier, corrective actions could have been taken to avoid the failure.

Moreover, the cost of installing and operating such mechanical seal systems can be prohibitive. First, the monitoring of conditions for high priority failure modes may require a customized advanced monitoring system designed specifically for the mechanical seal system to be monitored.

This is particularly true when the equipment to be monitored is unique or nonstandard, or where there are specific environmental conditions that require the system to be tailored to a particular application. Second, the operator of the advanced monitoring system must have the requisite knowledge in order to properly diagnose potential failures, which typically requires higher wages.

Accordingly, what is needed in the industry is a system and method that enables tailored customized advanced monitoring mechanical seal systems to be constructed and autonomously operated with improved reliability and increased speed, thereby alleviating the need for the mechanical seal system to be constantly monitored by a human operator during operation.

SUMMARY OF THE DISCLOSURE

Embodiments of the present disclosure meet the need of the industry for autonomous advanced monitoring mechanical seal systems and methods that offer improved reliability and increased speed, thereby alleviating the need for the mechanical seal system to be constantly monitored by a human operator having a requisite knowledge of the mechanical seal system in order to properly diagnose potential failures during operation. One embodiment of the disclosure includes a plurality of prefabricated failure mode logic modules. Each failure mode logic module can be configured to monitor data sensed by a plurality of sensors and diagnose conditions relating to one specific type of mechanical failure known to occur in mechanical seal systems. Through the use of multiple failure mode logic modules, numerous specific types of mechanical failures can be diagnosed. Select failure mode logic modules of the plurality of failure mode logic modules can be activated based on the likelihood of the occurrence of each specific type of mechanical failure actually occurring in the mechanical seal system.

To determine which of the plurality of failure mode logic modules should be activated for a system, the mechanical seal system can be evaluated, for example by FMEA, to determine which specific types of mechanical failures are most likely to occur. Thereafter, each of the plurality of the prefabricated failure mode logic modules can be activated or deactivated to suit individual customer needs, particular environmental conditions and/or specific applications of the mechanical seal system. Moreover, because the failure mode logic modules are pre-constructed, such that they can be activated when desired, installing such a system can be done at a fraction of the price of installing a system built from scratch.

Each activated failure mode logic module can employ logic and/or artificial intelligence algorithms configured to detect and analyze one or more operating conditions for the purpose of predicting a specific type of failure, as well as generally providing a real-time health assessment of the mechanical seal system. For example, an activated failure mode logic module can use the knowledge of which of the other failure mode logic modules are activated (i.e. which specific types of mechanical failures are most likely to occur) in its analysis of conditions relating to the specific type of mechanical failure to which it is designed to diagnose. Accordingly, each failure mode logic module can comprise a set of rules that enable the advanced monitoring system to properly diagnose failures and make conclusive determinations regarding the overall health of the mechanical seal system, without the need of a human operator with a requisite level of knowledge of the monitored mechanical seal system in order to properly diagnose failures and the overall health of the mechanical seal system. Accordingly, in one embodiment, the failure mode logic modules, through a complex set of rules, are configured to perform a function not previously performable by an advanced monitoring mechanical seal system.

One embodiment of the present disclosure provides a method of monitoring a mechanical seal system for the purpose of autonomously diagnosing a loss of lubrication within a sliding seal interface of the mechanical seal including: sensing acoustical emission data in proximity to the mechanical seal; establishing a baseline condition for the sensed acoustical emission data; sensing a temperature of lubrication fluid within or proximal to the sliding seal interface; establishing a baseline condition for the sensed temperature of the lubrication fluid within or proximal to the sliding seal interface; determining if the mechanical seal system is configured to diagnose a low flow of lubricating fluid provided to the sliding seal interface; determining if the sensed acoustical emission data exceeds the established baseline condition for the sensed acoustical emission data; determining if the sensed temperature of the lubrication fluid within or proximal to the sliding seal interface exceeds the established baseline condition for the sensed temperature of the lubrication fluid within or proximal to the sliding seal interface; determining if the mechanical seal system is configured to diagnose pressure reversal of the lubricating fluid; determining if the mechanical seal is configured to diagnose cavitation in proximity to the sliding seal interface; and sending a notification to a user that a loss of lubrication within the sliding seal interface is detected.

In one embodiment, the method further comprises evaluating the mechanical seal system to determine the likelihood of a failure of the mechanical seal system for at least one of a loss of lubrication within the sliding seal interface, a low-flow of lubricating fluid provided to the sliding seal interface, a pressure reversal of lubricating fluid proximal to the sliding seal interface, and cavitation occurring in proximity to the sliding seal interface. In one embodiment, the method further comprises tailoring the mechanical seal system to diagnose operating conditions related to mechanical seal system failures with a determined high likelihood of occurrence for the purpose of suiting individual customer needs, particular environmental conditions and/or specific applications of the mechanical seal system.

In one embodiment, the method further comprises activating a loss of lubrication failure mode logic module within the mechanical seal system, where the loss of lubrication failure mode logic module is configured to diagnose conditions relating to a loss of lubrication within the sliding seal interface. In one embodiment, the method further comprises activating at least one of a low-flow of lubricating fluid failure mode logic module, a pressure reversal of lubricating fluid failure mode logic module and a cavitation within the sliding seal interface failure mode logic module.

In one embodiment, the notification sent to the user indicates a severity of the loss of lubrication within the sliding seal interface. In one embodiment, the notification includes a recommendation message configured to provide the user guidance in order to troubleshoot and/or take appropriate action to remedy the loss of lubrication within the sliding seal interface. In one embodiment, the method further comprises starting a timer to determine an elapsed time after notification of the user. In one embodiment, the method further comprises sending an alarm message if the elapsed time exceeds a predefined period of time. In one embodiment, the predefined period of time is 30 minutes or less. In one embodiment the alarm message includes an estimated remaining useful life of the mechanical seal.

One embodiment of the present disclosure provides a mechanical seal system configured to autonomously detect a loss of lubrication within a sliding seal interface of a mechanical seal. The mechanical seal system can include a mechanical seal, one or more sensors, a loss of lubrication failure mode logic module, and a plurality of other failure mode logic modules. The mechanical seal can have a sliding seal interface between a stationary housing and a rotating shaft. The one or more sensors can be configured to sense acoustical emission data in proximity to the mechanical seal and a temperature of lubricating fluid within or in proximity to the sliding seal interface. The loss of lubrication failure mode logic module can be configured to monitor data sensed by the one or more sensors and diagnose conditions relating to a loss of lubrication within the sliding seal interface. The plurality of other failure mode logic modules can be configured to monitor data sensed by the one or more sensors and diagnose conditions relating to specific types of mechanical failures known to occur in mechanical seal systems. The plurality of other failure mode logic modules can include at least one of a low-flow of lubricating fluid failure mode logic module, a pressure reversal of lubricating fluid failure mode logic module and/or a cavitation in proximity to the sliding seal interface failure mode logic module. Select failure mode logic modules of the plurality of failure mode logic modules can be activated based on a likelihood of each failure mode logic module's respective specific type of mechanical failure actually occurring within the mechanical seal system. The loss of lubrication failure mode logic module can be configured to determine which of the plurality of other failure mode logic modules are activated during the diagnosis of conditions relating to a loss of lubrication within the sliding seal interface.

In one embodiment, select failure mode logic modules of the plurality of failure mode logic modules are activated for the purpose of tailoring the mechanical seal system to suit individual customer needs, particular environmental conditions and/or specific applications of the mechanical seal. In one embodiment, select failure mode logic modules of the plurality of failure mode logic modules are activated based on an evaluation of the mechanical seal system to determine the likelihood of a failure of the mechanical seal system for at least one of a loss of lubrication within the sliding seal interface, a low-flow of lubricating fluid provided to the sliding seal interface, a pressure reversal of lubricating fluid proximal to the sliding seal interface, and/or cavitation occurring in proximity to the sliding seal interface of the mechanical seal system.

One embodiment of the present disclosure provides a mechanical seal system having a customizable predictive diagnostic subsystem tailored to suit individual customer needs, particular environmental conditions and/or specific applications. The mechanical seal system can include a mechanical seal, a plurality of sensing devices, and a plurality of failure mode logic modules. The mechanical seal can be installed between a stationary housing and a rotatable shaft. The plurality of sensing devices can be configured to sense at least one of pressure, temperature, rotational speed, vibration, and acoustical emissions in proximity to the mechanical seal. The plurality of failure mode logic modules each can be configured to monitor data sensed by one or more of the plurality of sensing devices related to a specific type of mechanical failure known to occur in mechanical seals, and to provide notifications to a user regarding an actual occurrence of the specific type of mechanical failure in the mechanical seal system to a user via a user interface. Certain ones of the plurality of failure mode logic modules are selectively activated via the user interface for the purpose of tailoring the predictive diagnostic system to suit individual customer needs, particular environmental conditions and/or specific applications of the mechanical seal system.

In one embodiment, the specific type of mechanical failure is at least one of a loss of lubrication within the sliding seal interface of the mechanical seal, a low flow of lubricating fluid within the sliding seal interface, a pressure reversal of lubricating fluid proximal to the sliding seal interface, and/or cavitation occurring in proximity to the sliding seal interface.

In one embodiment, the mechanical seal system is at least one of an API Standard 01, 02, 11, 12, 13, 14, 21, 23, 31, 32, 41, 52, 53A, 53B, 53C, 54, 62, 65A, 65B, 66A, 66B 72, 74, 75, and/or 76 compliant system, or a combination thereof. In one embodiment, the mechanical seal system is operably coupled to a pump. In one embodiment, the mechanical seal includes at least one sliding seal interface into which a lubricating fluid is introduced. In one embodiment the mechanical seal system further includes a lubricating fluid conditioning unit including a heat exchanger and a bladder accumulator.

In one embodiment, at least one of the plurality of sensing devices includes at least one of a sensor configured to monitor acoustic emissions of the pump, a sensor configured to monitor vibrations and or rotational speed of the pump; a sensor configured to monitor the temperature of the pump; a sensor configured to monitor a temperature and/or pressure of lubricating fluid exiting the sliding seal interface; a sensor configured to monitor the temperature and/or pressure of lubricating fluid entering the sliding seal interface, a sensor configured to monitor acoustic emissions of the sliding seal interface, a sensor configured to monitor a temperature and/or pressure of lubrication fluid in or proximal to the sliding seal interface, a sensor configured to monitor a temperature and/or pressure of lubricating fluid proximal to the bladder accumulator, and/or a sensor configured to monitor a temperature and pressure of the lubricating fluid proximal to the heat exchanger.

In one embodiment, the plurality of sensing devices are operably coupled to one or more data aggregators configured to receive and process data sensed by one or more of the plurality of sensing devices and transmit data sensed by the one or more of the plurality of sensing devices to one or more server. In one embodiment the plurality of sensing devices are operably coupled to one or more data aggregators configured to receive and process data sensed by one or more of the plurality of sensing devices and transmit data sensed by the one or more of the plurality of sensing devices to one or more server, wherein the data sensed by the one or more plurality of sensing devices is transmitted wirelessly to the one or more server.

In one embodiment notifications include at least one of informal notifications, alert notifications, alarm notifications, trip notifications, and a recommendation message configured to provide the user guidance in order to troubleshoot and take appropriate action to existing conditions.

One embodiment of the present disclosure provides a mechanical seal system configured to detect operating conditions and provide real-time health assessments to a user during operation. The mechanical seal system can include a rotating device, a mechanical seal, a lubricating fluid conditioning unit, a plurality of sensors, and a plurality of failure mode logic modules. The rotating device can include a stationary housing and a rotating shaft. The mechanical seal can be configured to provide a sliding seal interface between the stationary housing in the rotating shaft of the rotating device. The lubricating fluid conditioning unit can be configured to introduce lubricating fluid into the sliding seal interface. The plurality of sensors can be configured to sense operating conditions of the mechanical seal. The plurality of failure mode logic modules can be configured to monitor the sensed operating conditions and provide feedback by way of notifications to a user via a user interface regarding a likelihood of specific types of mechanical failures occurring in the mechanical seal system. Each of the plurality of failure mode logic modules can be activated or deactivated to suit individual customer needs, particular environmental conditions and/or specific applications of the mechanical seal system.

One embodiment of the present disclosure provides a mechanical seal system having a predictive diagnostic subsystem configured to wirelessly communicate monitored conditions of a mechanical seal to an area remote from the potentially hazardous operating environment proximal to the mechanical seal. The mechanical seal system can include a mechanical seal, one or more sensing devices, a remotely located server, and a data aggregator. The mechanical seal can be installed between a stationary housing in a rotatable shaft. The one or more sensing devices can be configured to sense at least one of a pressure, temperature, rotational speed, vibration, and/or acoustic emissions in proximity to the mechanical seal. The remotely located server can be configured to collect and analyze data sensed by the one or more sensing devices. The data aggregator can be configured to wirelessly communicate the data sensed by the one or more sensing devices to the remotely located server. The data aggregator can include an explosion proof enclosure, one or more sensory input terminals, a signal processor, and an output interface. The one or more sensory input terminals can be configured to receive the data sensed by the one or more sensing devices. The signal processor can be configured to convert the data sensed by the one or more sensing devices to a digital signal. The output interface can be configured to wirelessly transmit the digital signal to the server.

In one embodiment, the data aggregator can be configured to receive data sensed by the one or more sensing devices in real time. In one embodiment, the explosion proof enclosure can be suitable for use within an Appareils destinés à être utilisés en Atmosphères Explosibles (ATEX) Zone 1 environment. In one embodiment, the enclosure can be water resistant. In one embodiment, the enclosure can be constructed of aluminum.

In one embodiment, the data aggregator can include a zener diode configured to limit electrical energy flowing into the potentially hazardous operating environment. In one embodiment the data aggregator can include a total of fourteen sensory input terminals. In one embodiment the sensor input terminals can include eight inputs for pressure and/or temperature sensors, three input terminals for vibration sensors, two input terminals for acoustic emission sensors, and one input terminal for a rotational speed sensor.

In one embodiment, the signal processor is configured to process data sensed by the one or more sensing devices to reduce the quantity of the data to be transmitted by the output interface. In one embodiment, the data aggregator further comprises a memory configured to store data sensed by the one or more sensing devices. In one embodiment, the output interface transmits the digital data to the server at least at scheduled times, random times and/or by request by the server.

One embodiment of the present disclosure provides a mechanical seal system configured to detect operating conditions and provide real-time health assessments to a user during operation. The mechanical seal system can include a mechanical seal, a plurality of sensors, a server, and a data aggregator. The mechanical seal can have a sliding seal interface between a stationary housing and a rotating shaft of a rotating device. The plurality of sensors can be configured to sense operating conditions of the mechanical seal system. The server can be configured to collect and analyze the sensed operating conditions. The data aggregator can be configured to wirelessly communicate the data sensed by the one or more sensing devices to the remotely located server. The data aggregator can include an explosion proof enclosure, one or more sensor input terminals, a signal processor, and an output interface. The one or more sensory input terminals can be configured to receive the sensed operating conditions. The signal processor can be configured to convert sensed operating conditions to a digital signal. The output interface can be configured to wirelessly transmit the digital signal to the server.

In embodiments, threshold values for comparison to sensed values are determined at least in part based on sensed data collected when the mechanical system is in a steady state. In embodiments, threshold values for comparison can be adjusted based on expected parameters determined by the design and known operation environment of the mechanical seal system. In embodiments, threshold values for comparison can be determined at least in part based on integrated seal performance simulation algorithms. In embodiments, threshold values for comparison can be determined without sensed data collected when the mechanical system is in a steady state.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which.

Figure 1:
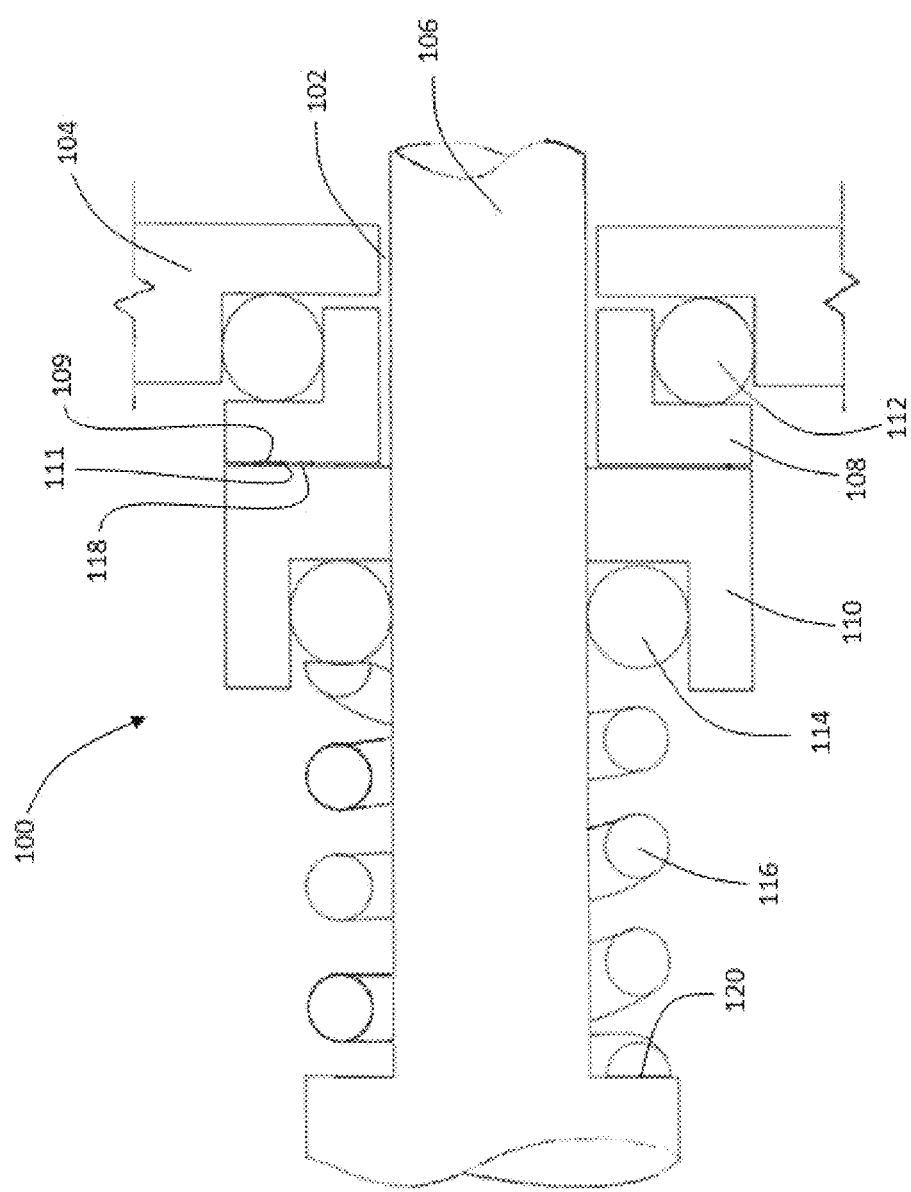
FIG. 1 is a partial, cross-sectional view depicting a mechanical seal of the prior art.

While embodiments of the disclosure are amenable to various modifications and alternative forms, specifics thereof are shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure as defined by the appended claims.

DETAILED DESCRIPTION

Referring to FIG. 1, a mechanical seal 100 according to the prior art is depicted. Details of the mechanical seal 100 are described in the Background section above. In other embodiments, mechanical seal 100 can be an American Petroleum Industry (API) Standard 682 compliant seal. The American Petroleum Industry standards represent the oil and natural gas industry's collective wisdom on environmental protection, sound engineering and operating practices and safe, interchangeable equipment and materials. The API Standards Program is accredited by the American National Standards Institute (ANSI), and many of the API standards have been incorporated into state and federal regulations.

Figure 2:
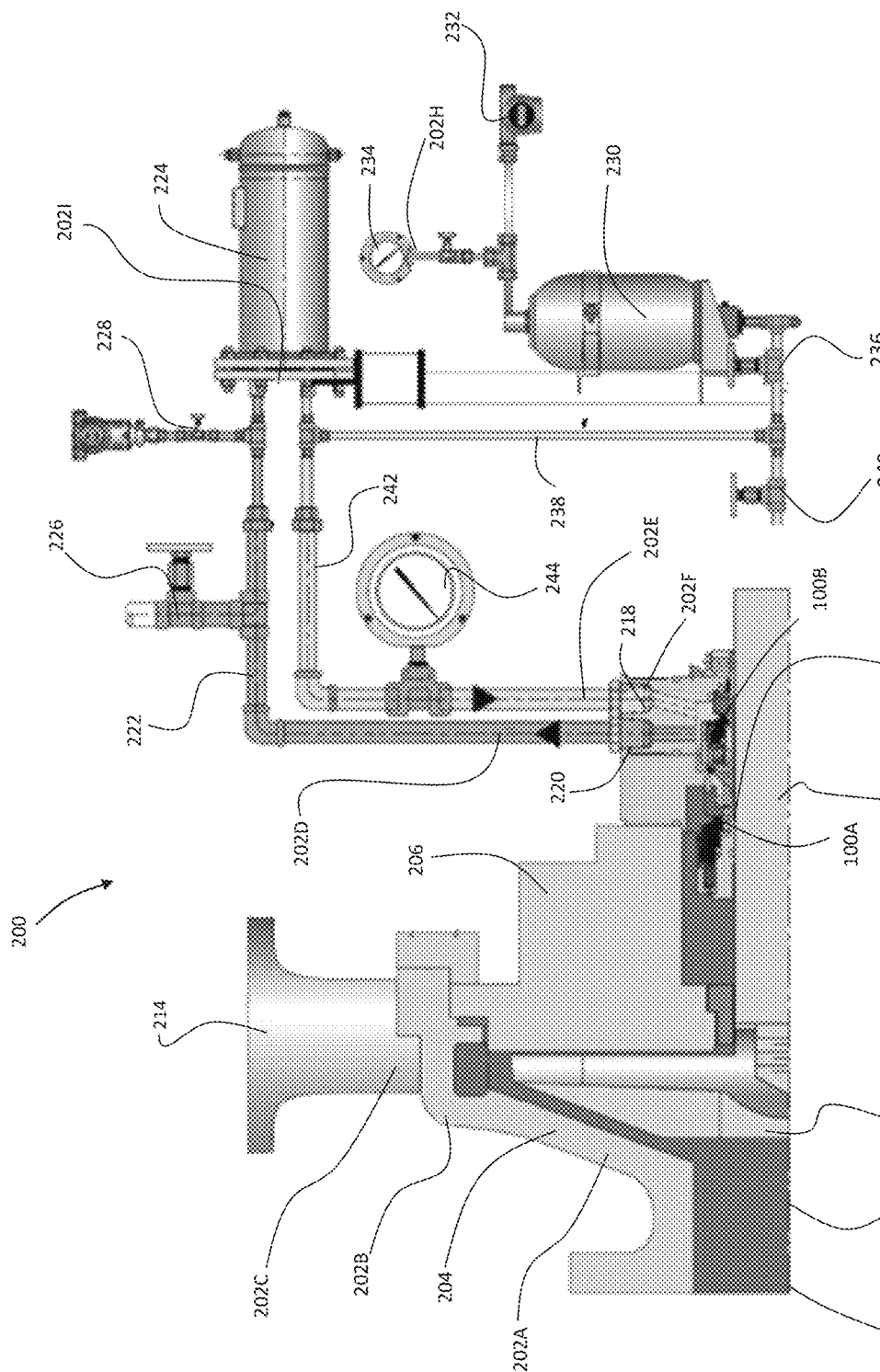
FIG. 2 is a partial, cross-sectional, elevation view depicting a mechanical seal system in accordance with an embodiment of the disclosure.
Figure 2A:
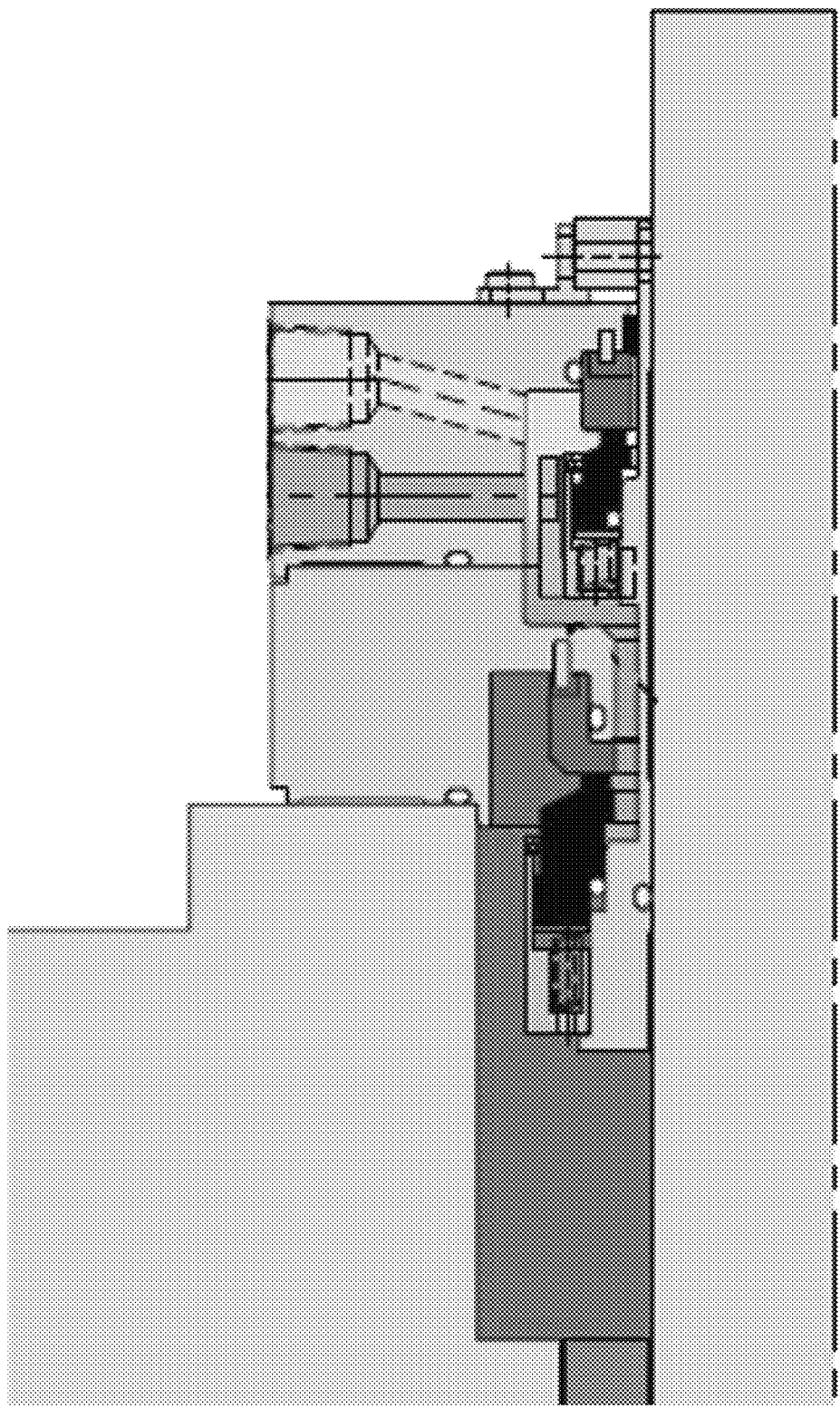
FIG. 2A is a partial, cross-sectional, elevation, detail view depicting a portion of the mechanical seal system of FIG. 2, in accordance with an embodiment of the disclosure.

Referring to FIG. 2, a mechanical seal system 200 including mechanical seal 100 is depicted in accordance with an embodiment of the disclosure. In this embodiment, mechanical seal system 200 is depicted as an American Petroleum Industry (API) Standard 53B compliant system. Other contemplated mechanical seal systems 200 include API Standard 01, 02, 11, 12, 13, 14, 21, 23, 31, 32, 41, 52, 53A, 53B, 53C, 54, 62, 65A, 65B, 66A, 66B, 72, 74, 75, and 76 compliant systems, or a combination thereof, such as a combination of API Standards 11 and 52. Further details of the API Standards and mechanical seal piping plans can be found in JOHN CRANE, MECHANICAL SEAL PIPING PLANS, POCKET GUIDE (4th ed.) (2016), the contents of which are incorporated by reference herein.

In one embodiment, the mechanical seal system can include a rotating machine 204, such as a centrifugal pump. Rotating machine 204 can include a housing 206. Housing 206 can define an internal compartment 208 configured to house an impeller 210. Internal compartment 208 can be in fluid communication with a suction nozzle 212 and a discharge nozzle 214. Impeller 210 can be operably coupled to a rotating shaft 216, which can be operably coupled to a drive mechanism (not depicted).

Fluid leakage and/or the introduction of contaminants into the fluid of internal compartment 208 can be inhibited by one or more mechanical seals 100. As depicted in FIG. 2, the mechanical seal system 200 includes two mechanical seals 100A/100B. In this embodiment, inboard seal 100A can be positioned proximal to the internal compartment 208, while the outboard seal 100B can be positioned proximal to a lubricating fluid inlet and outlet.

The heat and friction generated by the sliding seal interface 118 of both inboard and outboard seals 100A/100B can be cooled and lubricated by the introduction of a lubricating fluid. The lubricating fluid can enter the mechanical seal 100 at lubrication inlet 218 and exit the mechanical seals 100A/100B at lubrication outlet 220. Upon exiting the mechanical seal 100A/100B the lubricating fluid can pass through a conduit 222 to a heat exchanger 224. In one embodiment, the heat exchanger 224 can be configured to cool the lubricating fluid through heat transfer with a cooling fluid, such as water or air. Conduit 222 can include one or more events 226 and one or more lubrication bleed connections 228.

Fluid pressure can be applied to the lubricating fluid at the exit of the heat exchanger 224 by a bladder accumulator 230. Pressure from an external source can be applied to the bladder accumulator 230 through a bladder charge connection 232. Bladder accumulator 230 can include a pressure and/or temperature indicator 234 proximal to the bladder charge connection 232, for example, in the form of one or more gauges. Pressurized lubricating fluid can flow through a valve 236 into conduit 238. Conduit 238 can further include a valved lubricant fill connection 240.

The cooled and pressurized lubricating fluid can flow through a conduit 242 into lubrication inlet 218. Conduit 242 can further include one or more temperature, pressure and/or flow indicators 244 configured to provide a visual indication of the conditions of the cooled and pressurized lubricating fluid.

In one embodiment, the mechanical seal system 200 can include one or more sensors 202 configured to enable monitoring of the mechanical seal system 200 in real time. These sensors 202 can be intrusive or non-intrusive. For example, in one embodiment, one or more sensors 202 can be embedded in the mechanical seal 100, such as the sensors depicted in the dry seal arrangement of U.S. Pat. No. 8,651,801 (previously incorporated by reference). As depicted in FIG. 2, these sensors can include: a sensor configured to monitor acoustic emissions of the rotating machine 202A; a sensor configured to monitor vibrations and/or the rotational speed of the rotating machine 202B; a sensor configured to monitor a temperature of the rotating machine 202C; a sensor configured to monitor a temperature and/or pressure of lubricating fluid exiting the sliding seal interface (alternatively referred to as the outbound barrier fluid outlet temperature and/or pressure) 202D; a sensor configured to monitor the temperature and/or pressure of lubricating fluid entering the sliding seal interface (alternatively referred to as the inbound barrier fluid inlet temperature and/or pressure) 202E; a sensor configured to monitor acoustic emissions of the sliding seal interfaces 202F; a sensor configured to monitor a temperature and/or pressure of lubrication fluid in or proximal to the sliding seal interfaces (alternatively referred to as the barrier fluid temperature and pressure) 202G; a sensor configured to monitor a temperature and/or pressure of lubricating fluid proximal to the bladder accumulator 202H; and a sensor configured to monitor the temperature and pressure of lubricating fluid proximal to the heat exchanger 202I. Other sensors 202 and combinations thereof are also contemplated.

Figure 3:
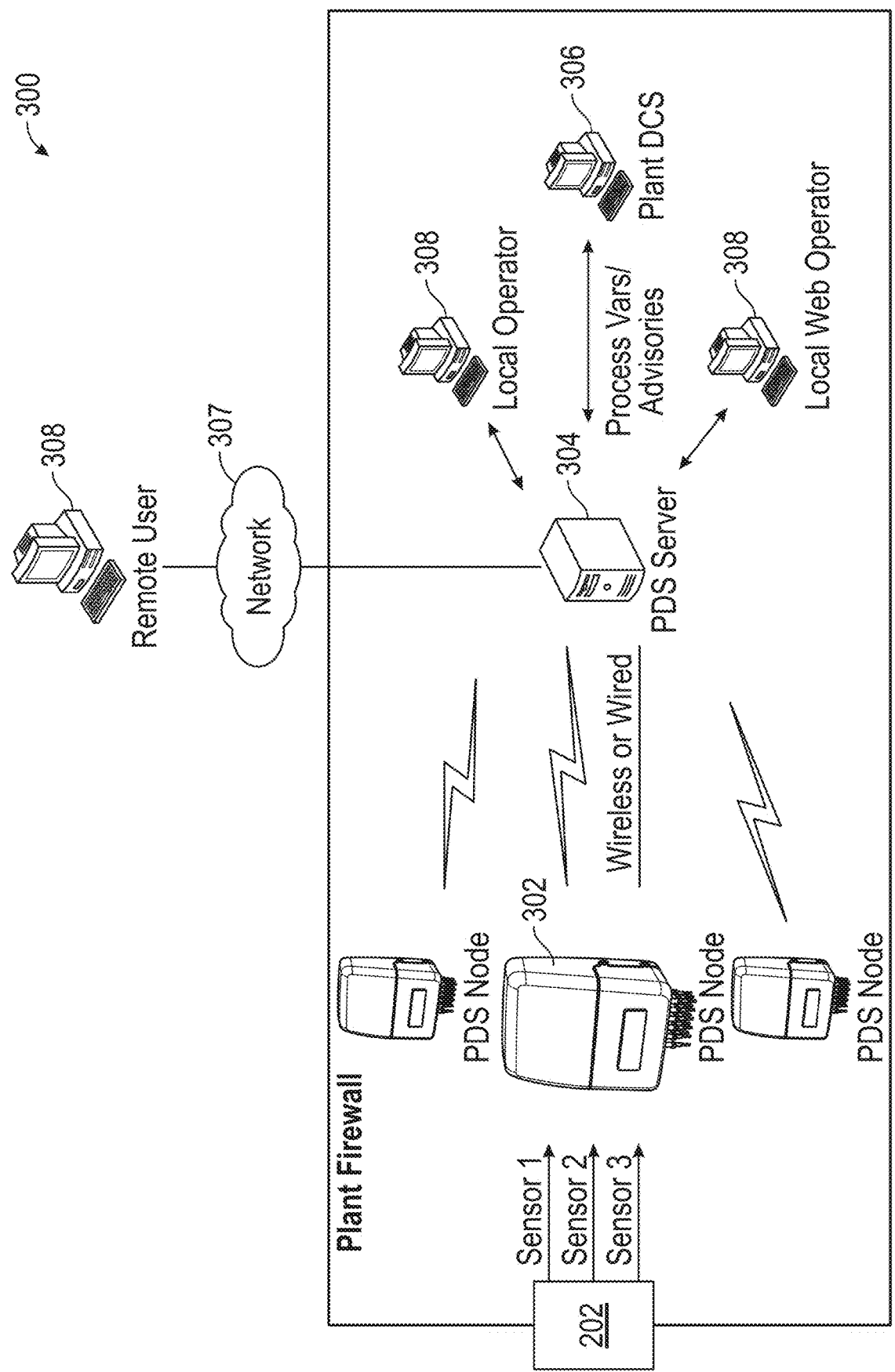
FIG. 3 is a schematic view depicting a predictive diagnostics subsystem in accordance with an embodiment of the disclosure.

Referring to FIG. 3, the mechanical seal system 200 can further include a predictive diagnostics subsystem 300, configured to monitor the overall health of the mechanical seal system 200 and provide an indication of impending failure. The one or more sensors 202 can be included as components of the predictive diagnostics system 300. For example, in one embodiment of the predictive diagnostics system 300, the one or more sensors 202 can be operably coupled to one or more data aggregators 302. Data aggregators can be configured to receive and process data sensed by the one or more sensors 202, and transmit the sensed data to one or more server 304. The server 304 can use the sensed data to make determinations regarding the health of the mechanical seal system 200, and provide alerts, notifications, and/or recommendation messages to control systems 306, such as a Plant Distributed Control System (DCS), and local operators or users 308. In one embodiment, the local operators 308 can be a local hardwired and/or wireless interface, or a remote and/or web-based interface. In one embodiment, server 304 can be in communication with a network 307 configured to communicate data to a remote user 308. The various communication links between components of the predictive diagnostics system 300 can be wired or wireless.

Figure 4:
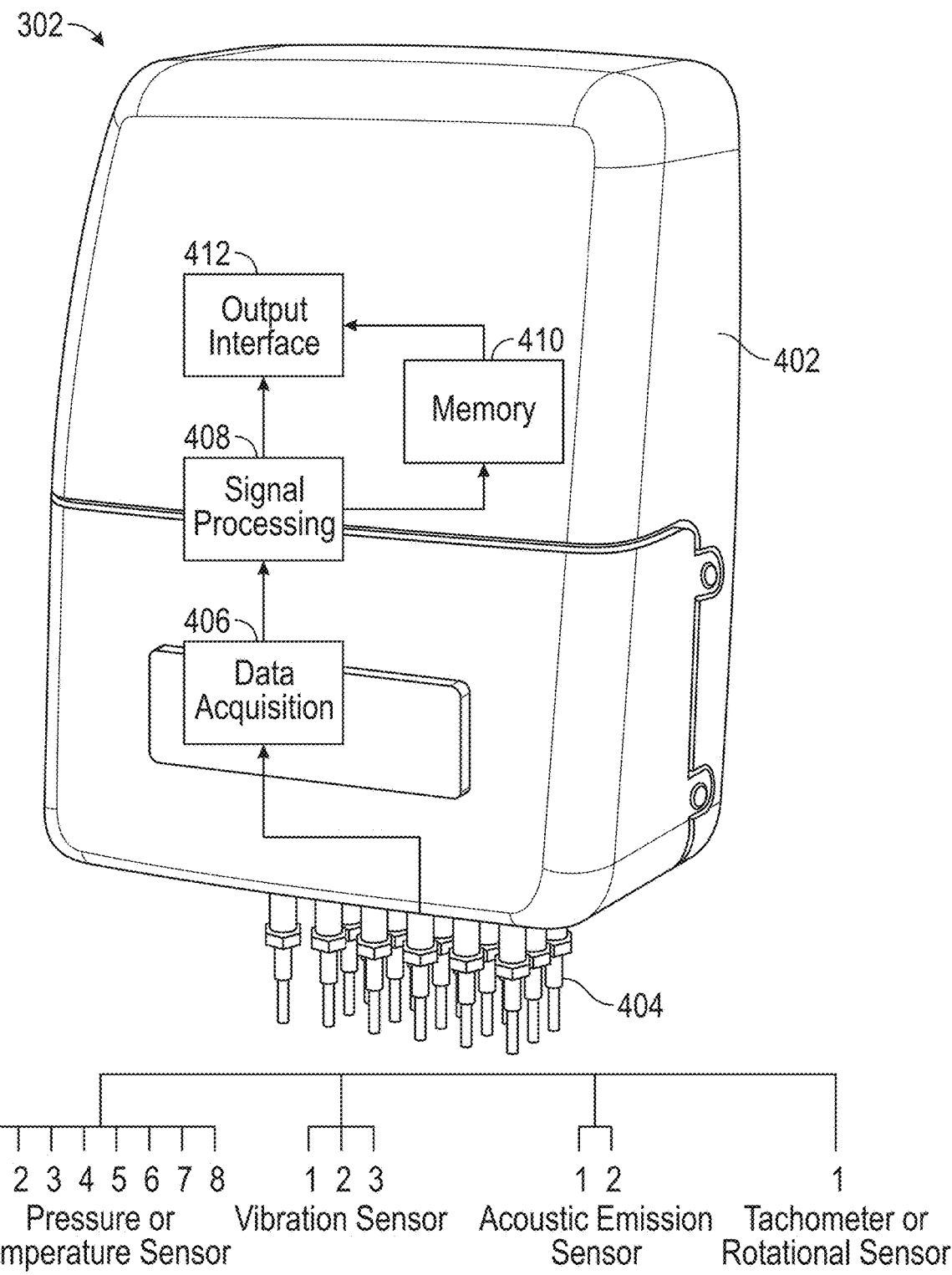
FIG. 4 is a block diagram depicting a data aggregator in accordance with an embodiment of the disclosure.

Referring to FIG. 4, a block diagram of a data aggregator 302 is depicted in accordance with an embodiment of the disclosure. Data aggregator 302 can be configured to receive data from sensors 202 in real-time and transmit the sensed data to server 304. In one embodiment, data aggregator 302 is contained within enclosure 402, which can serve to shield the internal components of data aggregator 302 from often harsh environmental conditions of its operating environment. For example, enclosure 402 can be explosion proof and/or suitable for use within an Appareils destinés à être utilisés en Atmosphères Explosibles (ATEX) Zone 1 environment (i.e., a place in which an explosive atmosphere consisting of a mixture with air of dangerous substances in the form of gas, vapor, or mist is likely to occasionally occur during normal operation). Explosion proof enclosure 402 can contain internal explosions to avoid igniting the surrounding atmosphere in embodiments. Enclosure 402 can also present environmental protections such as waterproofing or fireproofing. In one embodiment, enclosure 402 can be constructed of aluminum. In other embodiments, other materials providing sufficient environmental protection can be used.

In one embodiment, the data aggregator 302 can comprise a power input (not shown). In one embodiment, the power input can receive 24V DC. Other power inputs are also contemplated. In one embodiment, data aggregator 302 can include a safety diode (not shown), such as a zener diode which can limit electrical energy flowing into the dangerous environment through data aggregator 302.

In one embodiment, sensor input interface 404 can be a wired or wireless interface operably coupled to one or more sensors 202. Data acquisition engine 406 can include a high-speed data acquisition board, and can be configured to receive raw signals from the sensor input interface 404. In one embodiment, data acquisition engine 406 can support fourteen sensor channels for communication with fourteen sensors 202. For example, in one embodiment, the supported sensor channels can include eight 4-20 mA channels for standard sensors known in the art such as pressure sensors or temperature sensors, three channels for vibration sensors, two channels for acoustic emissions sensors, and one channel for a tachometer or rotational speed sensor.

Signal processing engine 408 can convert analog data received by the data acquisition engine 406 to digital signals. In one embodiment, the signal processing engine 408 conducts further signal processing to reduce the volume or quantity of data to be transmitted from the data aggregator 302.

In one embodiment, the digital signals from signal processing engine 408 can be queued in memory 410 for batch transmission to server 304 via output interface 412. In one embodiment, output interface 412 can provide digital signals at regularly scheduled times, random times, or by request from the server 304. In one embodiment, output interface 412 can comprise wired Ethernet connections, wireless connections via WiFi or other commercial off-the-shelf radio, or other direct wired connections such as universal serial bus (USB), parallel, or other direct cable connections. Because data aggregator 302 is physically configured to withstand inhospitable environments, other components of system 300, such as server 304 and clients 306 can be located in safer areas within, or external to, the hazardous working environment.

Figure 5:
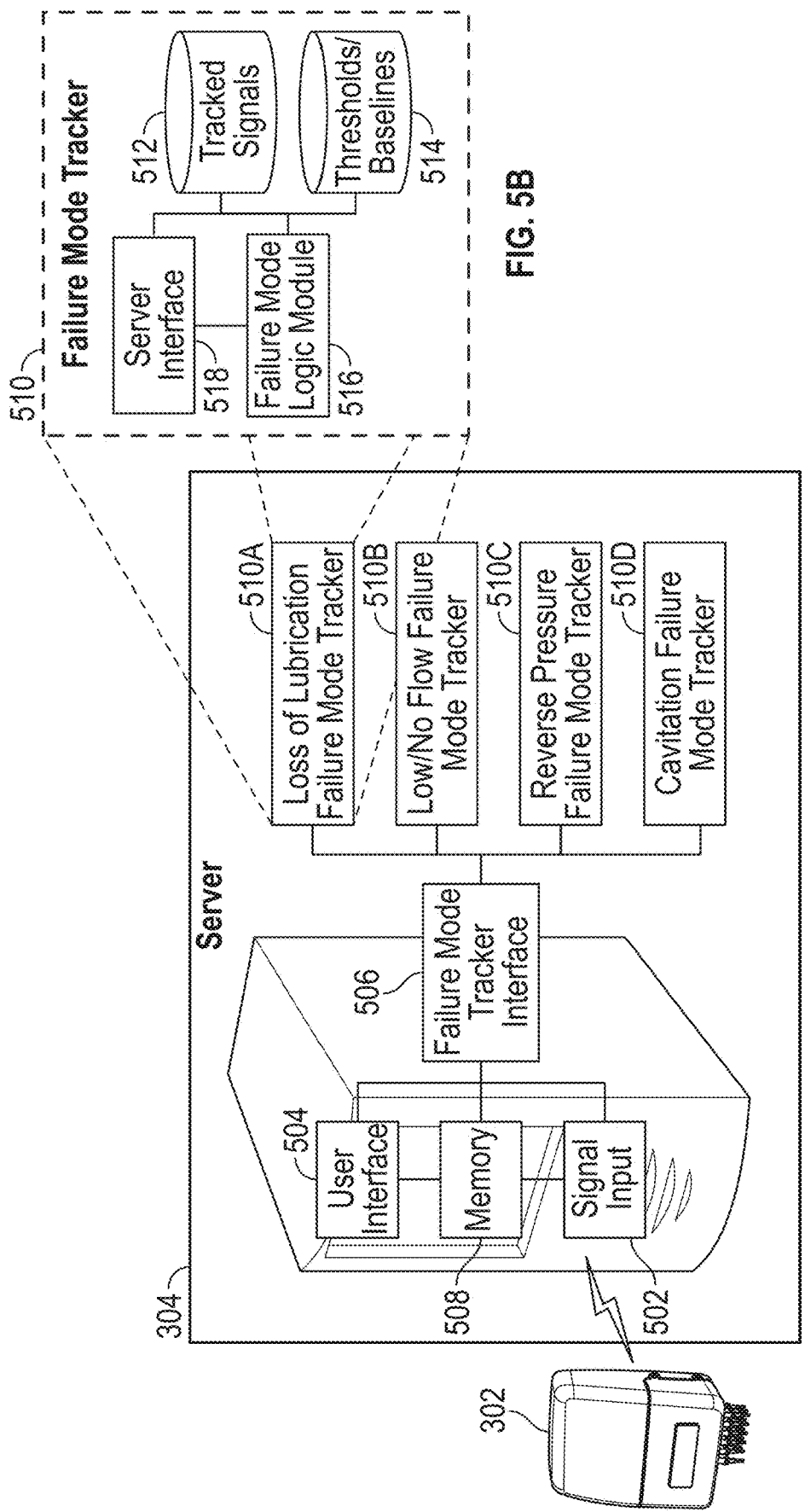
FIG. 5A-B are block diagrams depicting a server in accordance with an embodiment of the disclosure.

Referring to FIG. 5A, a block diagram depicting components of a server 304 is depicted in accordance with an embodiment of the disclosure. In one embodiment, server 304 can comprise a signal input engine 502, a user interface 504, a failure mode tracker interface 506, a memory 508, and one or more failure mode trackers 510.

Signal input engine 502 can receive data provided by one or more data aggregators 302. In one embodiment, the sensor data from one or more data aggregators 302 is received continuously by signal input engine 502. In other embodiments, the signal input engine 502 queries the one or more data aggregators 302 on a periodic basis. In another embodiment, the one or more data aggregators 302 push sensor data to the signal input engine 502 in the event of a predefined condition.

Memory 508 can be configured to temporarily or permanently store data received by signal input 502, as well as other data generated in the predictive diagnostics system 300, for example, data generated in the failure mode tracker interface 506 or the user interface 504.

User interface 504 can comprise input and output devices directly connected to server 304, and/or one or more remote client interfaces, such as web clients, mobile applications, or other interfaces to provide operator interaction with server 304. In one embodiment, user interface 504 can comprise an application programming interface permitting programmatic control and/or interaction with server 304. In one embodiment, the user interface 504 can push alerts, notifications of health conditions and/or recommendations to the plant DCS 306 and/or local or remote users/operators 308.

Failure mode tracker interface 506 can be configured to enable registration and activation of one or more failure mode trackers 510, as well as to communicate with activated failure mode trackers 510. Each failure mode tracker 510 can be configured to detect and analyze one or more operating conditions for the purpose of predicting one or more anticipated type of failure, as well as generally providing a real-time health assessment of the mechanical seal system 200. The specific failure mode trackers 510 that are registered and activated in each predictive diagnostics system 300 can depend on the specific system requirements and environmental conditions of the mechanical seal system 200 being monitored.

As depicted in FIG. 5A, in one embodiment, the predictive diagnostics system 300 can include a loss of lubricant failure mode tracker 510A, a low/no flow failure mode tracker 510B, a reverse pressure failure mode tracker 510C, and/or a cavitation failure mode tracker 510D. Other failure mode trackers 510 are also contemplated. Accordingly, registration and activation of select failure mode trackers 510 enables the predictive diagnostics system 300 to be tailored or customized to mechanical seal systems 200 to uniquely suit individual customer needs, particular environmental conditions or specific applications of the system 200.

Referring to FIG. 5B, each failure mode tracker 510 can be configured to receive sensor data via communication between the failure mode tracker interface 506 and a server interface 518. In some cases, the received sensor data can include a temporal element so as represent received sensor data over a period of time, which can be referred to as a tracked signal 512. In one embodiment, the failure mode tracker 510 can be configured to compare the tracked signals 512 with one or more predefined thresholds 514 according to a failure mode logic module 516. Alerts, notifications, recommendations, and/or other data can be generated by failure mode logic module 516, which can then be transmitted back to server 304 via server interface 518. In one embodiment, failure mode trackers can be arranged in one or more separate locations, whereby failure mode tracker interface 506 and server interface 518 are configured to communicate via network or direct communication links.

Failure mode trackers 510 encapsulate the logic and threshold criteria for individual failure modes, enabling server 304 to be configured with only the appropriate failure modes for a given mechanical seal system 200. In one embodiment, failure mode trackers 510 can be activated on server 304 at installation or during startup of the mechanical seal system 200. In one embodiment, failure mode trackers 510 can be activated or deactivated at any time. In one embodiment, configuration details can be received from server 304, or via configuration files stored locally, or at a remote network location. In one embodiment, server 304 can provide user interface elements enabling an operator to provide, modify, or delete configuration details. In one embodiment, server 304 can request an activation and/or condition status from one or more failure mode trackers 510 at any time.

Complex systems, such as pump system 200, can experience failures for multiple interrelated reasons. The potential failures for any mechanical seal system 200 can be specific to the design and operating environment of that seal system. Embodiments of the present disclosure can use results of FMEA or other diagnostics or prognostics analyses to identify potential failures. In addition, as actual failures or other incidents involving seal systems with similar attributes are analyzed, better predictions regarding any given seal system can be made.

Figure 6:
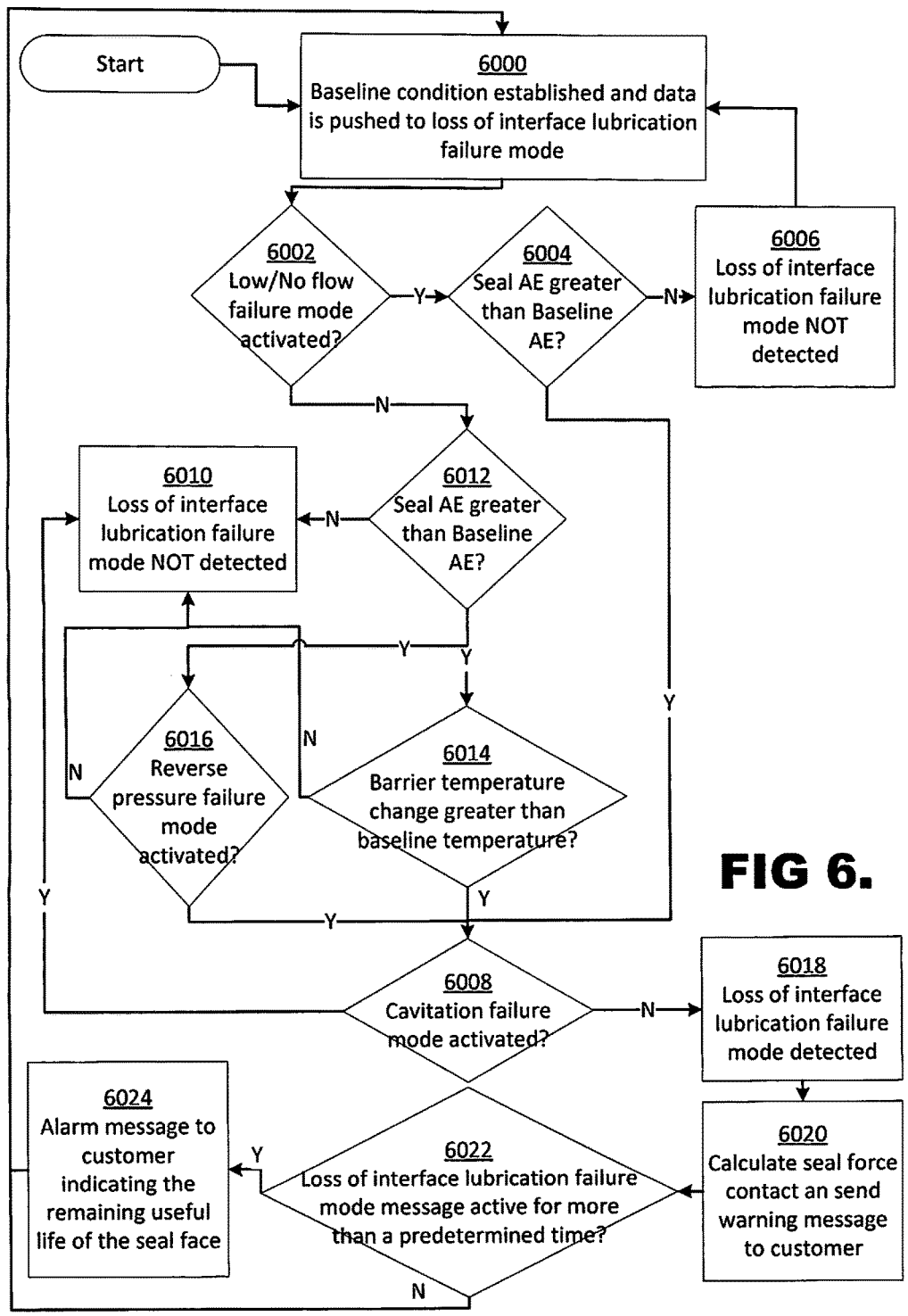
FIG. 6 is a flowchart depicting a loss of lubrication failure mode algorithm in accordance with an embodiment of the disclosure.

Referring to FIG. 6, a flowchart depicting an algorithm performed by the failure mode logic module 516 of a loss of lubrication failure mode tracker 510A is depicted in accordance with an embodiment of the disclosure. At 6000, steady state sensor data is transmitted by the failure mode tracker interface 506 and received by the server interface 518. Further details regarding establishing steady-state sensor data are discussed in connection with FIGS. 8-9

In one embodiment of the loss of lubrication failure mode tracker 510A, the received steady-state data can include acoustic emissions signals (of sensor 202F) and barrier fluid temperature signals (e.g., sensors 202D, 202E and/or 202G). The sensor data can further include a temporal element, so as to represent received sensor data over a period of time, which can be compiled or saved as a tracked signal 512. The tracked signal 512 can be communicated to the failure mode logic module 516.

In one embodiment, the failure mode tracker interface 506 further communicates the activation status of the failure mode trackers 510A-D within the predictive diagnostics system 300 to each activated failure mode tracker 510. For example, in one embodiment of the loss of lubrication failure mode tracker 510A, the failure mode tracker interface 506 communicates to the server interface 518 whether or not a low/no flow failure mode tracker 510B, a reverse pressure failure mode tracker 510C, and a cavitation failure mode tracker 510D have been activated.

At 6002, a determination is made as to whether the low/no flow failure mode tracker 510B has been activated. If the low/no flow failure mode tracker 510B has been activated, at 6004, an amplitude of the received seal acoustic emission signal is compared with an amplitude of an established baseline seal acoustic emission signal. If the amplitude of the received seal acoustic emission signal is less than or equal to the amplitude of the established baseline seal acoustic emission signal, at 6006 a determination is made that a loss of interface lubrication failure mode is not detected, and 6000 is repeated.

If the amplitude of the received seal acoustic emission signal is greater than the amplitude of the established baseline seal acoustic emission signal, at 6008 a determination is made as to whether the cavitation failure mode tracker 510D has been activated. If the cavitation failure mode tracker 510D has been activated, at 6010 a determination is made that a loss of interface lubrication failure mode is not detected, and 6000 is repeated. If the cavitation failure mode tracker 510D has not been activated, at 6018 a determination is made that a loss of interface lubrication failure mode is detected.

Returning to 6002, if the low/no flow failure mode tracker 510B has not been activated, at 6012 an amplitude of the received seal acoustic emission signal is compared with an established amplitude of the baseline seal acoustic emission signal. If the amplitude of the received seal acoustic emission signal is less than or equal to the amplitude of the established baseline seal acoustic emission signal, at 6010 a determination is made that a loss of interface lubrication failure mode is not detected, and 6000 is repeated.

If the amplitude of the received seal acoustic emission signal is greater than the amplitude of the established baseline seal emission signal, at 6014 a received barrier fluid temperature is compared with an established barrier fluid temperature baseline, and at 6016 a determination is made as to whether the reverse pressure tracker 510C has been activated. In one embodiment, these actions are performed simultaneously. If either the received barrier fluid temperature is less than or equal to the established barrier fluid temperature baseline, or the reverse pressure tracker 510C has not been activated, then at 6010 a determination is made that a loss of interface lubrication failure mode is not detected, and 6000 is repeated.

If the received barrier fluid temperature is greater than the established barrier fluid temperature baseline, and the reverse pressure tracker 510C has not been activated, the algorithm proceeds to 6008 to determine whether the cavitation failure mode tracker 510D has been activated. If the cavitation failure mode tracker 510D has been activated, at 6010 a determination is made that a loss of interface lubrication failure mode is not detected, and 6000 is repeated. If the cavitation failure mode tracker 510D has not been activated, at 6018 a determination is made that a loss of interface lubrication failure mode is detected.

If a determination is made that a loss of interface lubrication failure mode is detected, at 6020 a notification and/or recommendation message is sent to a user. At 6022 a timer is started to determine the elapsed time since the sending of the notification and/or recommendation message of 6020. If the elapsed time exceeds a predefined time limit and the appropriate actions have not been taken and/or the condition persists, at 6024 and alarm message is sent to the user. In one embodiment, the predefined time limit can be 30 minutes, although other predefined time limits are also contemplated. In one embodiment, the alarm message can indicate the remaining useful life of the seal face. If the appropriate actions are taken within the predefined time limit and/or the conditions for the detection of loss of interface lubrication failure mode subside, 6000 is repeated.

It should be understood that the individual steps used in the methods of the present teachings may be performed in any order and/or simultaneously, as long as the teaching remains operable. In one embodiment, other comparisons can be used. For example, where values to be compared are equal, within reasonable tolerance values, the values can be treated as if the first value is less than the second (as described above), or greater than the second.

In one embodiment, notifications can comprise informational notifications, alert notifications, alarm notifications, trip notifications, and/or recommendation messages which may provide a user or operator guidance in order to troubleshoot and/or take actions appropriate to existing conditions. The notifications may further indicate the severity of the reported condition and/or failure. In one embodiment, notifications can be delivered via plant DCS 306 and/or to local or remote operators 308 by a variety of systems, such as mobile phones, portable electronic devices, email, or other methods. In one embodiment, the delivery method of notifications can vary based on the severity of the notification.

In one embodiment, user interface 504 can enable one or more users to configure preferred notification locations and styles. User interface 504 can comprise one or more screens, each comprising one or more visual elements, including text, graphics, menus, windows, user input fields and/or other user interface elements.

Figure 7A:
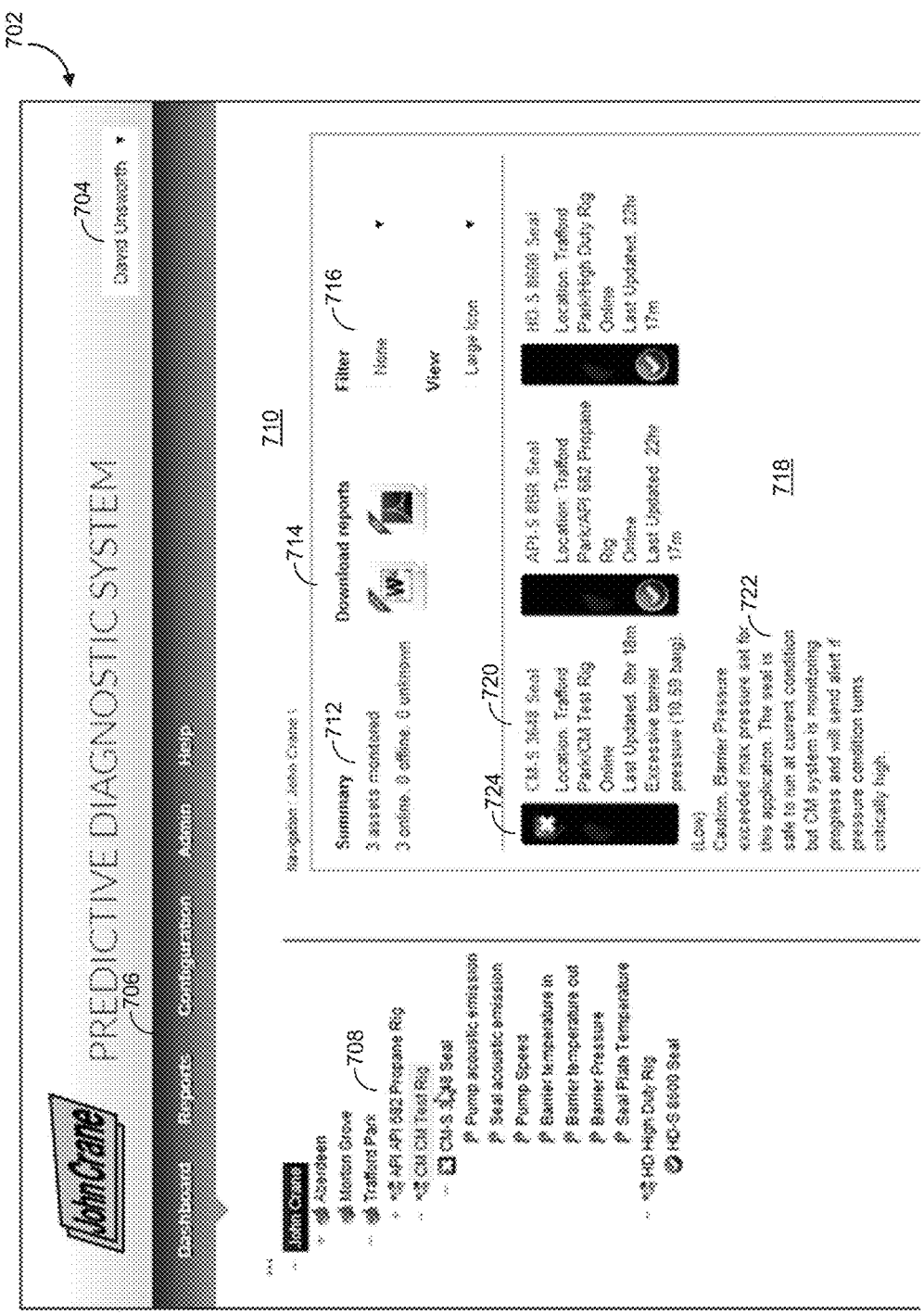
FIGS. 7A-B depict dashboard notifications and recommendations in accordance with an embodiment of the disclosure.
Figure 7B:
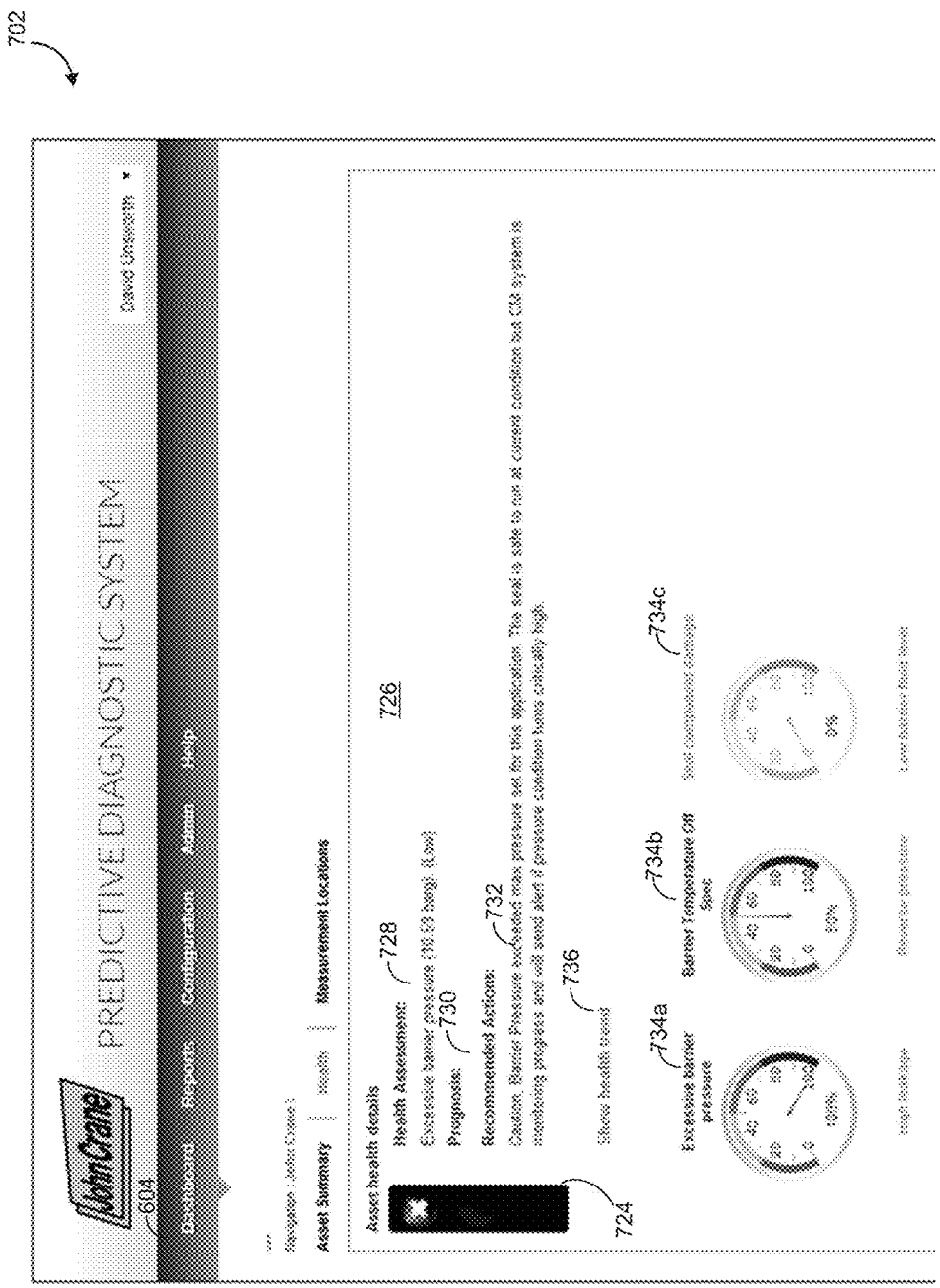

Referring to FIGS. 7A-B, dashboard notifications and recommendations 702 are depicted in accordance with an embodiment of the disclosure. In one embodiment, dashboard 702 can be customized by a user. User selection region 704, can display the currently logged in user, and enable different users to be selected. Dashboard 702 can further include menu 706, enabling navigation between one or more screens 702.

Depicted in FIG. 7A is a dashboard screen providing an overview of condition monitoring information for multiple seal systems. Navigation pane 708 includes a tree view displaying multiple seal systems grouped by location and associated device. In one embodiment, other organization schemes can be used, and can be selectable by the user. In one embodiment, only those seal systems reporting active alerts are displayed in navigation pane 708. As depicted in FIG. 7A, selection of a device can display summary screen 710, which can provide an overview of the condition of each seal system associated with the selected device. Summary region 712 can display summary information regarding the seal systems (or other assets) monitored. Report region 714 can enable the user to download reports in a user selected format such as Microsoft Word, or Portable Document Format (PDF). Other formats are also contemplated. Filter region 716 can enable the user to filter the displayed assets in order to simplify the view.

Details region 718 can display seal details 720 for the assets displayed by summary screen 710. Seal details 720 can include seal metrics, such as up-time, and location. Seal details 720 can also include notifications 722, if any, for each seal. Details region 718 can further include a status indicator 724 for each seal. As depicted in FIG. 7A, status indicator 724 can present a stop light element, where green indicates that no issues exist, and yellow and/or red indicate the presence of notifications of varying severity. Status indicator 724 can also include icons for differentiation of status levels such as a check mark for green, and an "X" indicating a red severity level.

FIG. 7B depicts a health assessment view 726 of a selected seal system in accordance with an embodiment of the disclosure. In one embodiment, health assessment view 726 can be accessed by selecting a seal system on summary screen 710 or navigation pane 708. Health assessment view 726 can include status indicator 724. Health assessment view 726 can also include a health assessment overview 728, which can include a brief summary of any current notification. Health assessment view 726 can include a prognosis 730, if prognosis information is available, and recommended actions 732 based on active notifications. Health assessment view 726 can further include one or more status indicators 734, presenting status indicators provided by one or more failure mode trackers 510. In one embodiment, inactive failure mode trackers can be presented as greyed out, such as 734c. In one embodiment, a health trend 736 can be provided, which can include health indications and notifications over a period of time.

Figure 8:
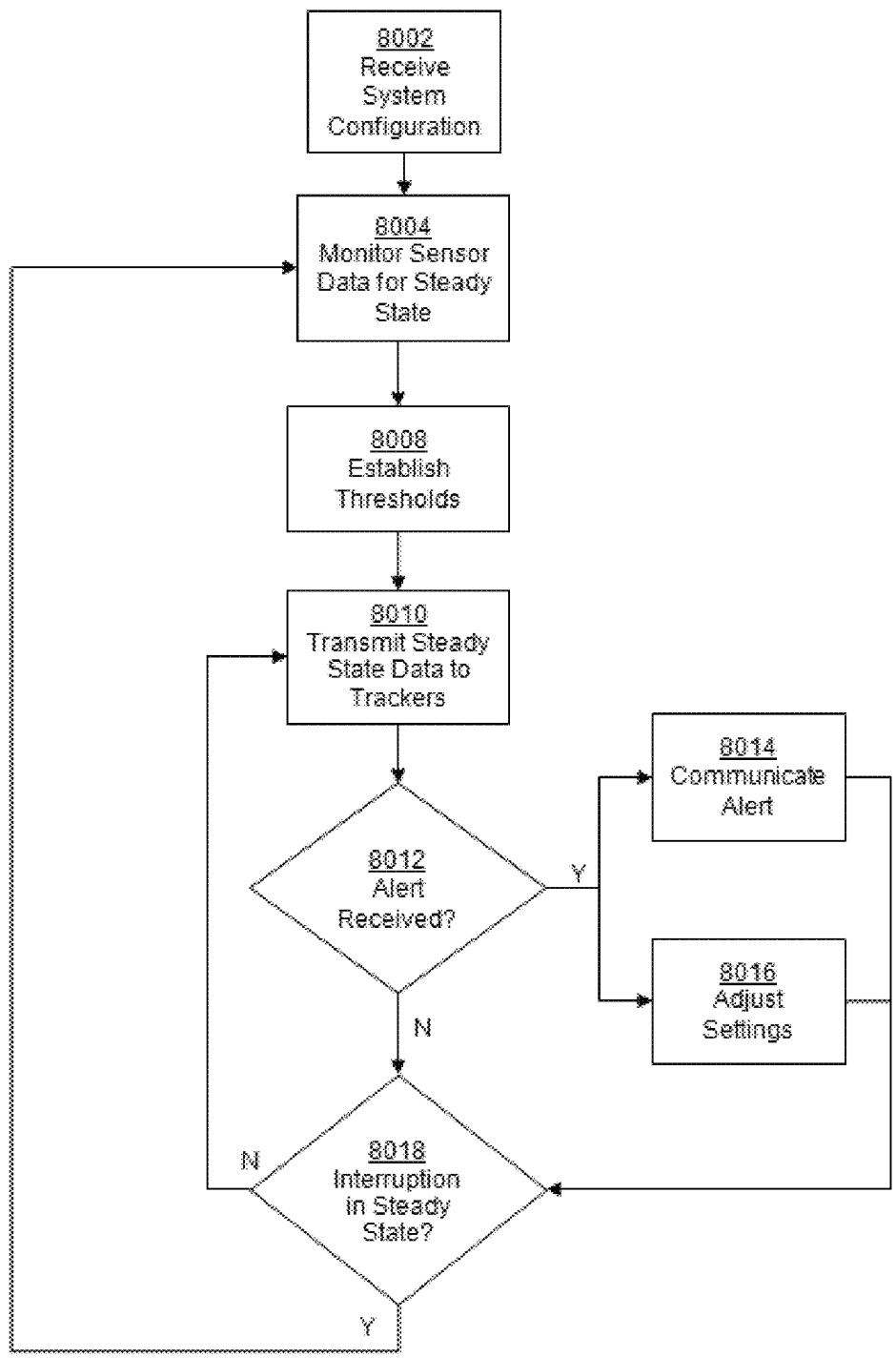
FIG. 8 depicts a method of operating a predictive diagnostics server in accordance with an embodiment of the disclosure.

Referring to FIG. 8, a method of operating the predictive diagnostics server 304 is depicted in accordance with an embodiment of the disclosure. At 8002, the predictive diagnostics system 300 configuration is received, for example from user interface 504 or memory 508. The predictive diagnostics system 300 configuration information can include, for example, environmental conditions and other attributes of the mechanical seal system 200 to be monitored and tracked, including the type and locations of the mechanical seals 100 and the types and locations of the various sensors 202. The predictive diagnostics system 300 configuration information can further include assignment and/or registration of one or more failure mode trackers 510 for each mechanical seal system 200, as well as a mapping and/or designation of the individual sensors 202 to be monitored or tracked by each failure mode tracker 510.

At 8004, the one or more sensors 202 are monitored for steady-state conditions, in which the conditions measured by each respective sensor 202 remains within a predefined normal operation tolerance window. Further details regarding the monitoring for steady-state conditions at 8004 are disclosed in FIG. 9 and the accompanying text. At 8008, the steady-state conditions established at 8004 can be used to establish a set of thresholds. In one embodiment, the established baselines and thresholds can be stored in a failure mode tracker 510 in memory 514.

At 8010, data from the one or more sensors 202 can be communicated to one or more assigned and/or registered failure mode trackers 510. The one or more failure mode trackers 510 can compare the sensor data to the established set of thresholds, and at 8012, where applicable, the one or more failure mode trackers 510 can issue an alert or notification that a particular threshold has been exceeded.

The failure mode tracker 510 can push the notification to failure mode tracker interface 506. At 8014, the notification can be communicated to a user, and/or at 8016 recommendations for adjusting the mechanical seal system 200 can be communicated to a user. In one embodiment, the notification and/or recommendations for adjusting the mechanical seal system 200 can be communicated to the user via user interface 504. For example, in one embodiment, the alert, notification and/or recommendations can be communicated by dashboards 702 (as depicted in FIGS. 7A-B).

Based on the conditions indicated at 8012, 8014 and/or 8016, the one or more assigned and/or registered failure mode trackers 510 can compare the sensor data to establish baseline conditions to determine whether there has been an interruption in the steady-state monitored sensor conditions at 8018. If the monitored sensor conditions remain in a steady-state, 8010 can be repeated. While steady state continues, data can be transmitted to failure mode trackers 510 at 8010 indefinitely. Alternatively, if the monitored sensor conditions are no longer in a steady-state, 8004 can be repeated for the purpose of establishing a set of new baselines and/or a new set of thresholds.

Figure 9:
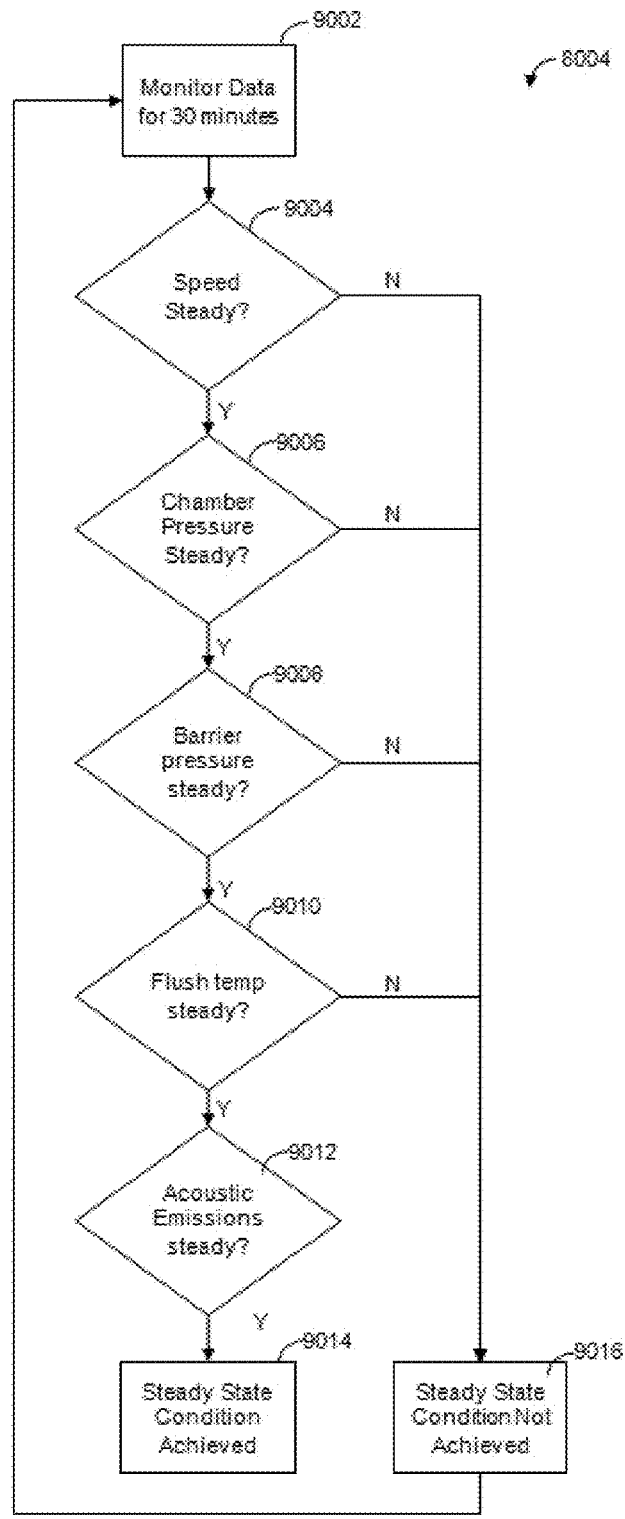
FIG. 9 depicts a method of detecting steady state conditions in a mechanical seal system in accordance with an embodiment of the disclosure.

Referring to FIG. 9, the step of monitoring sensor data for a steady-state 8004 is depicted in accordance with an embodiment of the disclosure. At 9002, signal data is monitored for a predefined monitoring period. In one embodiment, the monitoring period is 30 minutes. In other embodiments, the monitoring period may be longer or shorter than 30 minutes. At 9004, 9006, 9008, 9010, and 9012, various monitored conditions, as sensed by the one or more sensors 202, are evaluated to determine if they have deviated during the monitoring period. In one embodiment, the signals monitored can be rotation speed of the rotating shaft (measured the a sensor 202B), chamber pressure (i.e., a pressure of the lubrication fluid on either side of the sliding seal interface) (measured via sensors 202D and 202E), barrier pressure (i.e., a pressure of the lubrication fluid within or proximal to the sliding seal interface) (measured via sensor 202G), and flush temperature (i.e., a temperature of the lubrication fluid exiting the mechanical seal) (measured via sensor 202D), acoustical emissions (measured via sensor 202F). Alternative signals may be monitored as appropriate.

In one embodiment, steady state for each of signals 9004, 9006, 9008, 9010, and 9012 can be determined by checking whether the monitored conditions remain within 10 percent of a computed moving average of the monitored conditions during the monitoring period. In other embodiments, other methods for determining whether the monitored conditions remain within a predefined normal operating tolerance window can be employed.

If any of signals 9004, 9006, 9008, 9010, and 9012 are not steady, at 9016 a steady state is deemed to be not achieved during the monitoring period, and 9002 can be restarted. Alternatively, if all of signals 9004, 9006, 9008, 9010, and 9012 are steady, at 9014 the mechanical seal system 200 can be considered to be in a steady state.

Accordingly, in a steady-state, the mechanical seal system 200 waits until the sensed conditions are "settled" to acquire baseline data unique to the duty conditions in which the mechanical seals are operating. The baseline data is then used to establish or adjust the threshold values required to make health assessments of the mechanical seal system 200.

In embodiments, the threshold values can be determined based on, at least in part, intergrade (or integrated) seal performance simulation algorithms, such as those known in the art. Seal performance simulation algorithms can generate one or more sets of expected parameters. In embodiments, failure mode modules can compare the expected parameters to baseline data, if available, in order to determine threshold values. This integration enables the determination of threshold values that consider detected deviations from a theoretical ideal system, as modeled by seal performance simulation algorithms, and the actual running conditions of the system.

Figure 10:
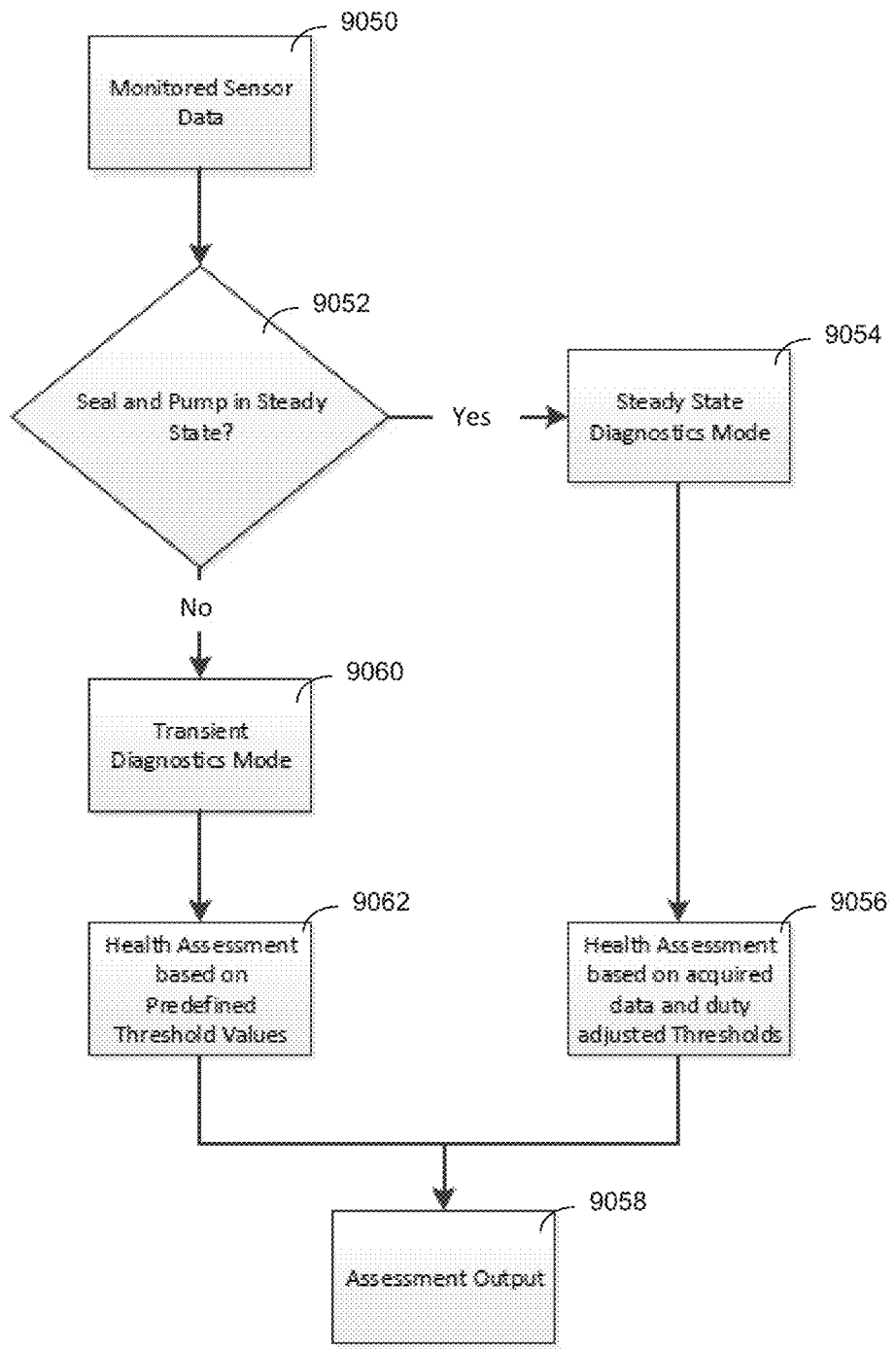
FIG. 10 depicts a method of enabling a mechanical seal system to monitor and alert operators of a critical condition in a transient mode, before steady state conditions are established, in accordance with an embodiment of the disclosure.

Referring to FIG. 10, a method of enabling the system 200 to monitor and alert operators of a critical condition in a transient mode, prior to reaching steady-state conditions or during changes in the duty cycle before a new steady-state condition can be established, is depicted in accordance with an embodiment of the disclosure. While some failure mode logic modules work independently from the existence of threshold values, other failure mode logic modules depend on established thresholds to alert operators of operation outside of safe operational limits. In the transient mode, the baseline data is not available to adjust the threshold values; instead, the mechanical seal system 200 utilizes predefined threshold values in order to provide an estimate of the mechanical seal health.

At 9050, signal data is monitored for a predefined monitoring period. At 9052, a determination is made as to whether the mechanical seal and pump are in a steady-state. If the mechanical seal and pump are in a steady-state, at 9054, the mechanical seal system 200 enters into a steady-state diagnostics mode. At 9056, health assessments can be made based on acquired data and duty adjusted thresholds, wherein the thresholds can be established, for example, through the process depicted in FIG. 9. Thereafter, at 9058, system assessment outputs can be delivered to a user.

Alternatively, if the mechanical seal and the pump are not in a steady-state, at 9060, the mechanical seal system 200 enters into a transient diagnostic mode. At 9062, health assessments can be made based on predefined threshold values. Thereafter, at 9058, system assessment outputs can be delivered to a user.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

In one embodiment, the predictive diagnostic system 300 and/or its components or subsystems can include computing devices, microprocessors, modules and other computer or computing devices, which can be any programmable device that accepts digital data as input, is configured to process the input according to instructions or algorithms, and provides results as outputs. In one embodiment, computing and other such devices discussed herein can be, comprise, contain or be coupled to a central processing unit (CPU) configured to carry out the instructions of a computer program. Computing and other such devices discussed herein are therefore configured to perform basic arithmetical, logical, and input/output operations.

Computing and other devices discussed herein can include memory. Memory can comprise volatile or non-volatile memory as required by the coupled computing device or processor to not only provide space to execute the instructions or algorithms, but to provide the space to store the instructions themselves. In one embodiment, volatile memory can include random access memory (RAM), dynamic random access memory (DRAM), or static random access memory (SRAM), for example. In one embodiment, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the disclosure.

In one embodiment, the system or components thereof can comprise or include various modules or engines, each of which is constructed, programmed, configured, or otherwise adapted to autonomously carry out a function or set of functions. The term "engine" as used herein is defined as a real-world device, component, or arrangement of components implemented using hardware, such as by an application specific integrated circuit (ASIC) or field programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Moreover, reference in the specification to "one embodiment," "an embodiment," or "some embodiments" means that a particular feature, structure, or characteristic, described in connection with the embodiment, is included in at least one embodiment of the teaching. The appearances of the phrase "in one embodiment" in various places in the specification are not necessarily all referring to the same embodiment.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. A method of monitoring a mechanical seal system for the purpose of autonomously diagnosing a loss of lubrication within a sliding seal interface of a mechanical seal, the method comprising:
    sensing acoustical emission data in proximity to the mechanical seal;
    establishing a baseline condition for the sensed acoustical emission data;
    sensing a temperature of lubrication fluid proximal to sliding seal interface;
    establishing a baseline condition for the sensed temperature of the lubrication fluid proximal to the sliding seal interface;
    determining if the mechanical seal system is configured to diagnose a low flow of lubricating fluid provided to the sliding seal interface;
    determining if the sensed acoustical emission data exceeds the established baseline condition for the sensed acoustical emission data;
    determining if the sensed temperature of the lubrication fluid proximal to the sliding seal interface exceeds the established baseline condition for the sensed temperature of the lubrication fluid proximal to the sliding seal interface;
    determining if the mechanical seal system is configured to diagnose a pressure reversal of the lubricating fluid;
    determining if the mechanical seal system is configured to diagnose cavitation in proximity to the sliding seal interface; and
    sending a notification to a user that a loss of lubrication within the sliding seal interface is detected.

2. The method of claim 1, further comprising evaluating the mechanical seal system to determine the likelihood of a failure of the mechanical seal system for at least one of a loss of lubrication within the sliding seal interface, a low-flow of lubricating fluid provided to the sliding seal interface, a pressure reversal of lubricating fluid proximal to the sliding seal interface, and cavitation occurring in proximity to the sliding seal interface of the mechanical seal system.

3. The method of claim 2, further comprising tailoring the mechanical seal system to diagnose operating conditions related to mechanical seal system failures with a determined high likelihood of occurrence for the purpose of suiting individual customer needs, particular environmental conditions and/or specific applications of the mechanical seal system.

4. The method of claim 2, further comprising activating a loss of lubrication failure mode logic module within the mechanical seal system, wherein the loss of lubrication failure mode logic module is configured to diagnose conditions related to a loss of lubrication within the sliding seal interface.

5. The method of claim 2, further comprising activating at least one of a low-flow of lubricating fluid failure mode logic module, a pressure reversal of lubricating fluid failure mode logic module, and a cavitation in proximity to the sliding seal interface failure mode logic module.

6. The method of claim 1, wherein the notification sent to the user indicates a severity of the loss of lubrication within the sliding seal interface.

7. The method of claim 6, wherein the notification includes a recommendation message configured to provide the user guidance in order to troubleshoot and/or take appropriate action to remedy the loss of lubrication within the sliding seal interface.

8. The method of claim 6, further comprising starting a timer to determine an elapsed time after notification of the user.

9. The method of claim 8, further comprising sending an alarm message if the elapsed time exceeds a predefined period of time.

10. The method of claim 9, wherein the predefined period of time is 30 minutes or less.

11. The method of claim 9, wherein the alarm message includes an estimated remaining useful life of the mechanical seal.

12. A method of monitoring the health condition of one or more seals in a mechanical seal system with respect to expected parameters based on integrated seal performance simulation algorithms, for the purpose of autonomously diagnosing an operational anomaly within the mechanical seal system, the method comprising:

sensing operational parameter data in proximity to the mechanical seal system;

establishing baseline condition parameters based on the sensed operational parameter data when the sensed operational parameter data indicates that the mechanical seal system is in a steady state;

establishing baseline condition parameters based on the expected parameters when the sensed operational parameter data indicates that the mechanical seal system is not in a steady state; and comparing the baseline condition parameters to the operational parameter data.

13. A method as claimed in claim 12, said step of sensing operational parameter data in proximity to the mechanical system comprising sensing operational parameter data within the mechanical seal system.

* * * * *